(12) United States Patent
Zhou et al.

(10) Patent No.: US 11,827,878 B2
(45) Date of Patent: Nov. 28, 2023

(54) **CONSTRUCTION OF RECOMBINANT *SACCHAROMYCES CEREVISIAE* FOR SYNTHESIZING CARMINIC ACID AND APPLICATION THEREOF**

(71) Applicant: Jiangnan University, Wuxi (CN)

(72) Inventors: Jingwen Zhou, Wuxi (CN); Qian Zhang, Wuxi (CN); Song Gao, Wuxi (CN); Jian Chen, Wuxi (CN); Weizhu Zeng, Wuxi (CN); Guocheng Du, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/818,389

(22) Filed: Aug. 9, 2022

(65) Prior Publication Data

US 2023/0127135 A1 Apr. 27, 2023

Related U.S. Application Data

(63) Continuation of application No. PCT/CN2021/114793, filed on Aug. 26, 2021.

(30) Foreign Application Priority Data

Aug. 28, 2020 (CN) .......................... 202010888117.3

(51) Int. Cl.
*C12N 1/18* (2006.01)
*C12N 9/12* (2006.01)
*C12N 15/81* (2006.01)

(52) U.S. Cl.
CPC .............. *C12N 1/185* (2021.05); *C12N 9/12* (2013.01); *C12N 15/815* (2013.01); *C12Y 207/00* (2013.01)

(58) Field of Classification Search
None
See application file for complete search history.

(56) References Cited

U.S. PATENT DOCUMENTS

2019/0127767 A1* 5/2019 Møller .................... C12P 17/06

FOREIGN PATENT DOCUMENTS

| CN | 111187786 A | 5/2020 |
|----|-------------|--------|
| CN | 111979134 A | 11/2020 |
| WO | 2018148849 A1 | 8/2018 |
| WO | 2019241322 A1 | 12/2019 |

OTHER PUBLICATIONS

Wattanachaisaereekul et al., "Optimization of Heterologous Production of the Polyketide 6-MSA in *Saccharomyces cerevisiae*", Biotechnology and Bioengineering, vol. 97, No. 4, Jul. 1, 2007.*
Bond et al., "*Saccharomyces cerevisiae* as a tool for mining, studying and engineering fungal polyketide synthases", Fungal Genetics and Biology, vol. 89, pp. 52-61, 2016. doi:10.1016/j.fgb.2016.01.005.*
Rasmus J.N. et. al., "Heterologous production of the widely used natural food colorant carminic acid in Aspergillus nidulans", Scientific Reports, vol. 8, Issue 12853,Aug. 27, 2018.
Kim J.M. et. al., "Characterization of NpgA a 4"-phosphopantetheinyl transferase of Aspergillus nidulans and evidence of its involvement in fungal growth and formation of conidia and cleistothecia for development", Journal of Microbiology, vol. 53, Issue 1,Dec. 31, 2015.
Oberegger H. et. al., "4"-Phosphopantetheinyl transferase-encoding npgA is essential for siderophore biosynthesis in Aspergillus nidulans", Current Genetics, V44, Dec. 31, 2003.
Zhao, FY et. al. "Research on brewing process of new grape vinegar" Food and Fermentation Industries, vol. 45. No. Dec. 31, 2019.

* cited by examiner

*Primary Examiner* — Suzanne M Noakes
(74) *Attorney, Agent, or Firm* — IPRO, PLLC; Na Xu

(57) ABSTRACT

The disclosure discloses construction of recombinant Saccharomyces cerevisiae for synthesizing carminic acid and application thereof and belongs to the technical field of genetic engineering and bioengineering. The disclosure obtains recombinant *S. cerevisiae* CA-B2 capable of synthesizing carminic acid by heterologously expressing cyclase ZhuI, aromatase ZhuJ, OKS of Octaketide synthase 1, C-glucosyltransferase UGT2, monooxygenase aptC and 4'-phosphopantetheinyl transferase npgA in *S. cerevisiae*. The recombinant *S. cerevisiae* can be used for synthesizing carminic acid by taking self-synthesized acetyl-CoA and malonyl-CoA as a precursor. On this basis, OKS, cyclase, aromatase, C-glucosyltransferase and monooxygenase relevant to carminic acid are integrated to a high copy site, which can remarkably improve the yield of carminic acid. The yield of carminic acid can be increased to 2664.6 μg/L by optimizing fermentation conditions, and the fermentation time is shortened significantly. Therefore, the recombinant *S. cerevisiae* plays an important role in the fields of cosmetics, textiles and food.

10 Claims, 7 Drawing Sheets

Specification includes a Sequence Listing.

24-deep-well plates

SEQUENCE LISTING

```
Sequence total quantity: 82
SEQ ID NO: 1            moltype = DNA  length = 1035
FEATURE                 Location/Qualifiers
misc_feature            1..1035
                        note = Synthetic DNA
source                  1..1035
                        mol_type = other DNA
                        organism = synthetic construct
SEQUENCE: 1
atggttcaag atacttcttc agcttctaca tcaccaatct tgactagatg gtacatcgat   60
acaagaccat taactgcttc tacagctgca ttgccattgt tagaaacttt acaaccagca  120
gatcaaattt cagttcaaaa gtactaccat ttgaaggata agcatatgtc tttggcatca  180
aatttgttga agtacttgtt cgttcataga aactgtagaa tcccatggtc ttcaattgtt  240
atttctagaa caccagatcc acatagaaga ccatgttata ttccaccatc tggttcacaa  300
gaagattctt ttaaagatgg ttacactggt attaatgttg aattcaatgt ttctcatcaa  360
```

```
gcttcaatgg ttgctattgc aggtactgct tttactccaa attctggtgg tgactcaaag    420
ttgaagccag aagttggtat cgatatcaca tgtgttaacg aaagacaagg tagaaatggt    480
gaagaaagat ctttggaatc attgagacaa tacatcgata ttttctctga agttttctct    540
actgctgaaa tggcaaacat cagaagattg gatggtgttt cttcatcttc attgtctgct    600
gatagattgg ttgattacgg ttacagattg ttttatacat actgggcttt gaaggaagca    660
tacatcaaga tgactggtga agctttgtta gcaccatggt tgagagaatt ggaatttcta    720
aacgttgttg ctccagctgc agttgcagaa tctggtgact cagctggtga ctttggtgaa    780
ccatatacag tgttagaaac tacattgtac aagaatttgg ttgaagatgt tagaatcgaa    840
gttgctgcat tgggtggtga ctatttgttt gctactgctg caagaggtgg tggtattggt    900
gcatcttcaa gaccaggtgg tggtccagat ggttctggta ttagatcaca agatccatgg    960
agaccttta  agaaattgga tatcgaaaga gatatccaac catgtgctac aggtgtttgt   1020
aattgtttat cttaa                                                    1035

SEQ ID NO: 2           moltype = DNA  length = 1212
FEATURE                Location/Qualifiers
misc_feature           1..1212
                       note = Synthetic DNA
source                 1..1212
                       mol_type = other DNA
                       organism = synthetic construct
SEQUENCE: 2
atgtcctctt tgtccaacgc ttcccatttg atggaagatg ttcaaggtat tagaaaagct     60
caaagagctg atggtactgc taccgttatg gctattggta ctgctcatcc accacacatt    120
tttccacaag atacttacgc tgatttctat tttcgtgcca ctaattctga acataaagtc    180
gaattgaaga agaagttcga tagaatttgt aagaagacca tgattggtaa aagatacttt    240
aactatgatg aagaattctt gaagaagtat ccaaacatta cttcctttga gaaccatct    300
ttgaacgata gacaagatat ttgtgttcca ggtgttccag cattaggtgc tgaagctgct    360
gttaaggcta tagctgaatg gggtagacca agtctgaaa ttactcactt agttttctgc    420
acttcttgtg tgttgacat gccttccgct gacttccaat gtgctaagtt gttgggtttg    480
agaaccaatg ttaataagta ctgtgtatac atgcaagtt gttacgccgg tgtgtaccgtt    540
atgagatacg ctaaggactt ggctgaaaat aacagaggtg ctagagtttt ggttgtctgt    600
gctgaattaa ccatcattgg tttgagaggt ccaaacgaat ctcatttgga taatgctatt    660
ggtaactctt tgtttggtga cggtgctgct gctttaattg ttggttctga tccaattatt    720
ggtgttgaaa agcaatgtt tgaaattgtt tgtgctaaac aaactgttat tccaaactct    780
gaagatgtta tccatttgca catgagagaa ctggtttaa tgttctacat gtcaaaggat    840
tcaccagaaa ctatctctaa caacgttgaa gcttgtttgg ttgatgtctt taagtcggtt    900
ggtatgactc ctcagaaga ttggaactct tgttctgga ttccacatcc aggtggtaga    960
gctattttag atcaagtcga agctaaattg aaattgagac cagaaaagtt cagagctacc    1020
agaaccgttt tgtgggattg tggtaacatg tgtctccgct gttttgta tattttggat    1080
gaaatgagac gtaagtctgc tgatgaaggt ttggaaactt atggtgaagg tttgaatgg    1140
ggtgtttat tgggtttcgg tcctggtatg actgttgaaa ctattttgtt gcattctttg    1200
ccattgatgt aa                                                       1212

SEQ ID NO: 3           moltype = DNA  length = 510
FEATURE                Location/Qualifiers
misc_feature           1..510
                       note = Synthetic DNA
source                 1..510
                       mol_type = other DNA
                       organism = synthetic construct
SEQUENCE: 3
atgagacatg ttgaacatac tgttactgtc gctgctccag ctgatttggt ttgggaagtt     60
ttggctgatg tcttgggtta cgctgatatt ttcccaccaa ctgaaaaggt tgaaattttg    120
gaagaaggtc aaggttacca agttgttaga ttacatgttg atgttgctgg tgaaattaac    180
acttggactt ctagacgtga tttggatcca gctagaagtg ttattgctta tagacaattg    240
gaaaccgctc caattgttgg tcatatgtct ggtgaatgga gagctttcac tttagatgct    300
gaaagaactc aattggttt  gactcatgat tttgttacta gagctgctgg cgatgatggt    360
ttggttgctg gtaaattgac tccagatgaa gctagagaaa tgttggaagc tgttgttgaa    420
agaaattctg ttgctgattt gaacgctgtt ttgggtgaag ctgaaagaag agttagagct    480
gctggtggtg ttggtactgt tactgcttaa                                     510

SEQ ID NO: 4           moltype = DNA  length = 771
FEATURE                Location/Qualifiers
misc_feature           1..771
                       note = Synthetic DNA
source                 1..771
                       mol_type = other DNA
                       organism = synthetic construct
SEQUENCE: 4
atgtctggta aaagactttt cttggatttg tctttcgcta ctagagatac tccatctgaa     60
gctactccag ttgttgttga tttgttggat catgttactg gtgctactgt tttgggtttg    120
tctccagaag attttccaga tggtatggct atttctaacg aaactgttac tttgactact    180
cataccggta ctcacatgga tgctccattg cattatggtc cattgtctgg tggtgttcca    240
gctaagtcta ttgatcaagt tccattggaa tgtggttaca ggtcaggtgt tagattggat    300
gttagacacg ttccagccgg tgacggtatt accgttgatc atttgaacgc tgcttttgat    360
gctgctgaac acgactggcc tccaggtgac atcgttatgt tgtggactgg tgctgatgct    420
ttgtggggta ctagagaata cttgtctacc ttcccaggtt tgactggtaa aggtacccaa    480
ttcttggttg aagctggtgt taaggttatt ggtattgatg cctggggttt ggatagacca    540
atggctgcta tgattgaaga atacagaaga actggtgaca agggtgcttt gtggccagct    600
```

```
catgtttatg gtagaactag agaatacttg caattagaaa agttgaataa cttgggtgct    660
ttgccaggtg ctactggtta tgatatctct tgttttccag ttgctgttgc tggtactggt    720
gctggtggtgga ctagagttgt tgctgttttc gaacaagaag aagaagatta a            771
```

SEQ ID NO: 5             moltype = DNA   length = 1548
FEATURE                  Location/Qualifiers
misc_feature             1..1548
                         note = Synthetic DNA
source                   1..1548
                         mol_type = other DNA
                         organism = synthetic construct
SEQUENCE: 5
```
atggaattca gattattgat tttggctttta ttctctgttt tgatgtctac ttccaacggt    60
gctgaaattt tagctttatt cccaattcac ggtatttcta actataacgt tgctgaagcc   120
ttattgaaga ctttggctaa cagaggtcat aatgtcaccg tcgttacttc ctttccacag   180
aaaaagccag ttcctaattt gtatgaaatt gatgttagtg gtgctaaggg tttagccact   240
aactcaattc atttcgaaag attgcaaact attattcaag atgtcaagtc taatttcaaa   300
aacatggtta gattgtccag aacttactgt gaaatcatgt tctctgatcc aagagtttta   360
aacattagag ataaaaagtt tgacttggtc atcaatgctg tttttggttc tgattgtgac   420
gctggttttg cttggaaatc ccaagctcca ttgatctcaa ttttaaatgc tagacatact   480
ccatgggctc tacatcgtat gggtaaccca tctaatccag cctacatgcc agttattcat   540
tctagattcc cagttaaaat gaacttttcc caaagaatga ttaacactgg ttggcatcta   600
tacttcttgt acatgtattt ctactacggt aatggtgaag atgctaacaa gatggctaga   660
aagttcttcg gtaatgatat gccagatatt aatgaaatgg tttttaatac ttctttattg   720
tttgttaaca ctcactttct tgttgatatg ccatacccac tcgttccaaa ctgtattgaa   780
attggtggta ttcacgttaa ggaaccacaa ccattgcaat tagaaatcca aaaattcatg   840
gatgaagctg aacatggtgt tatcttcttt actttgggtt ctatggttag aacttctact   900
ttcccaaatc aaacaatcca agctttcaaa gaagctttcg ctgaattgcc acaaagagtt   960
ttgtggaagt tgaaaatgaa aaacgaagat atgccatcta acgttttaat tcgtaaatgg  1020
tttccacaaa acgatatttt cggtcataaa aatattaagg ttttttattag tcatggtggt  1080
aactctggtg ctttggaagc tgttcatttc ggtgtcccaa tcattggtat ccctttgttc  1140
tacgatcaat atagaaacat tttgtctttt gttaaggaag agttgccgt tctgttggat   1200
gttaacgatt tgactaagga taacattttg tcttctgtta gaaccgtggt caatgataag  1260
tcatactctg aacgtatgaa ggccttgtct caattgttta gagatcgtcc aatgtctcca  1320
ttggataccg ccgtgtattg gactgaatat gtcattagac acagaggtgc ccaccaccta  1380
aagaccgctg gtgctttctt gcactggtac caatacttgt tattgatgt tatcactttc   1440
ttgttggtta ctttctgtgc tttctgcttt attgttaaat acatttgtaa ggctttgatt  1500
catcattact ggtcttcttc taagtctgaa aagttgaaga gaactaa                1548
```

SEQ ID NO: 6             moltype = DNA   length = 1254
FEATURE                  Location/Qualifiers
misc_feature             1..1254
                         note = Synthetic DNA
source                   1..1254
                         mol_type = other DNA
                         organism = synthetic construct
SEQUENCE: 6
```
atgactttgc cagtttttgat tattggtgct ggtttgtctg tttgactac tgctagattg    60
ttaactaacg ctcatattcc atgtattgtt ttcgaagctt ctcctcctc tagaactcaa   120
ggttacgcta tttcttacg tgattgggg tttaatgctt tattgagagc tttaggtaac   180
ttgccattat cttcattgac tagagctgtt gctccagata gacacattgg tggttgggac   240
tggttagatc aatcctggcg taataatcaa actggtgaaa tcattatgat gccaccaaag   300
gaatctaagg aaaagccaac cattttgaga gctaatagaa atgctttgag acaatgggatt   360
gctgatgctg tgttggtga agatgaagaa ttgacgtta gatatggtca tagattagtt   420
ggtgttcaat tgttaagaga aggtggcgat ggtaatgttg tcaccgctga attcgcaaac   480
ggtgctactt acaccggttc tttattgatc gctgctgatg tgttcattc tactgttaga   540
acttaatttt tgcctgctgt taagccagaa attttgccag ttttggtcta tcatggcgat   600
ttcagttaa gtagagaaga atacgaatgt gtcattagac acatgctgg tgaatctacc   660
attgttgctg tgttggtga cggtttcaac actccactaa ctgttttgtga cgttacttcc   720
actacagttc atatggattg gacttactct agaccatcta ttggcgataa cgatccattg   780
tacaatccta acattacttc tgaagaagct aaagttatcc ctgaggcttt gattgaagaa   840
attaatgcta agaagttagg tgaaccatgg tccttgtttt tgaatggtga agctatgaga   900
agacatagag ttttttaactg gttgactcgt tgtgtttcaa tggaaagatc tgacgttaac   960
tcttgtaccg gcaagggtgt tgttttttgtt ggagattctt ggcattttc gccaattttc  1020
ggtggtgaag tggtaaccca tgccattttt gatggtatcg aattagctaa gatgttgaa   1080
gttgcttggg tcgttccaa ggaagatgtt caagctgcta ttggtaaata ctatgataag  1140
tcttggagaa gatgtaacga cgctgttcgt agatccaagc aaagattcta ccaattgcat  1200
agaccaattt ccgaatggat tgaaatcgct gaaaagcaaa gatgagagc ttaa          1254
```

SEQ ID NO: 7             moltype = DNA   length = 509
FEATURE                  Location/Qualifiers
misc_feature             1..509
                         note = Synthetic DNA
source                   1..509
                         mol_type = other DNA
                         organism = synthetic construct
SEQUENCE: 7
```
gaagacgatg aggccggtgc cgatgtgccc ttgatggaca caaacaaca gctctcttcc     60
ggccgtactt agtgatcgga acgagctctt tatcaccgta gttctaaata acacatagag   120
```

```
taaattattg ccttttcttt cgttcctttt gttcttcacg tcctttttat gaaatacgtg    180
ccggtgttcc ggggttggat gcggaatcga agtgttgaa tgtgaaatat gcggaggcca    240
agtatgcgct tcggcggcta aatgcggcat gtgaaaagta ttgtctattt tatcttcatc    300
cttctttccc agaatattga acttatttaa ttcacatgga gcagagaaag cgcacctctg    360
cgttggcgg aatgttaatt tgagacgtat ataaattgcc gctttcgtca cctttttttg     420
gcttgttctg ttgtcgggtt cctaatgtta gtttatcct tgatttattc tgtttcattc     480
ccttttttt ccagtgaaaa agaagtaac                                       509

SEQ ID NO: 8            moltype = DNA  length = 188
FEATURE                 Location/Qualifiers
misc_feature            1..188
                        note = Synthetic DNA
source                  1..188
                        mol_type = other DNA
                        organism = synthetic construct
SEQUENCE: 8
attgaattga attgaaatcg atagatcaat ttttttcttt tctctttccc catcctttac    60
gctaaaataa tagtttattt tatttttga atatttttta ttttatatac tatatataga    120
ctattattta tctttaatg attattaaga ttttattaa aaaaaaattc gctcctcttt    180
taatgcct                                                             188

SEQ ID NO: 9            moltype = DNA  length = 530
FEATURE                 Location/Qualifiers
misc_feature            1..530
                        note = Synthetic DNA
source                  1..530
                        mol_type = other DNA
                        organism = synthetic construct
SEQUENCE: 9
gaaaccacac cgtggggcct tgttgcgcta ggaataggat atgcgacgaa gacgcttctg    60
cttagtaacc acaccacatt ttcaggggt cgatctgctt gcttccttta ctgtcacgag    120
cggcccataa tcgcgctttt ttttaaaag gcgcgagaca gcaaacagga agctcgggtt    180
tcaaccttcg gagtggtcgc agatctggag actggatctt tacaatacag taaggcaagc    240
caccatctgc ttcttaggtg catgcgacgg tatccacgtg cagaacaaca tagtctgaag    300
aaggggggga ggagcatgtt cattctctgt agcagtaaga gcttggtgat aatgaccaaa    360
actggagtct cgaaatcata taaatagaca atatattttc acacaatgag atttgtagta    420
cagttctatt ctctctcttg cataaataag aaattcatca agaacttggt ttgatatttc    480
accaacacac acaaaaaaca gtacttcact aaatttacac acaaaacaaa                530

SEQ ID NO: 10           moltype = DNA  length = 725
FEATURE                 Location/Qualifiers
misc_feature            1..725
                        note = Synthetic DNA
source                  1..725
                        mol_type = other DNA
                        organism = synthetic construct
SEQUENCE: 10
tttgccagct tactatcctt cttgaaaata tgcactctat atcttttagt tcttaattgc    60
aacacataga tttgctgtat aacgaatttt atgctatttt ttaaatttgg agttcagtga    120
taaaagtgtc acagcgaatt tcctcacatg tagggaccga attgtttaca agttctctgt    180
accaccatgg agacatcaaa aattgaaat ctatggaaat atggacgg tagcaacaag       240
aatatagcac gagccgcgga gttcatttcg ttacttttga tatcactcac aactattgcg    300
aagcgcttca gtgaaaaaat cataaggaaa agttgtaaat attattggta gtattcgttt    360
ggtaaagtag aggggtaat ttttccccctt tattttgttc atacattctt aaattgcttt    420
gcctctcctt ttgaaaagct atacttcgga gcactgttga gcgaaggctc attagatata    480
ttttctgtca ttttccttaa cccaaaaata agggaagg tccaaaaagc gctcggacaa     540
ctgttgaccg tgatccgaag gactggctat acagtgttca caaatagcc aagctgaaa     600
taatgtgtag ctatgttcag ttagtttggc tagcaaagat ataaaagcag gtcggaaata    660
tttatgggca ttattatgca gagcatcaac atgataaaa aaaacagttg aatattccct    720
caaaa                                                                725

SEQ ID NO: 11           moltype = DNA  length = 279
FEATURE                 Location/Qualifiers
misc_feature            1..279
                        note = Synthetic DNA
source                  1..279
                        mol_type = other DNA
                        organism = synthetic construct
SEQUENCE: 11
tcacatatga aagtatatac ccgcttttgt acactatgta gctataattc aatcgtatta    60
ttgtagctcc gcacgaccat gccttagaaa tatccgcagc gcgcaaaagg cggcctcgca    120
ttggcccaat tagctccggt gtaaaaaggg caaacttata taaggggatt aatgactttc    180
tatgagaatg ccaaaaaatg ttaggctaaa ggaagggatt gaaggaata tagttgagct    240
atactttctt gaaatactgg agtatacata tttataggg                           279

SEQ ID NO: 12           moltype = DNA  length = 6332
FEATURE                 Location/Qualifiers
misc_feature            1..6332
                        note = Synthetic DNA
```

| | | |
|---|---|---|
| source | 1..6332 | |
| | mol_type = other DNA | |
| | organism = synthetic construct | |

SEQUENCE: 12

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc   180
accataccac agcttttcaa ttcaattcat cattttttt ttattctttt ttttgatttc   240
ggtttctttg aaattttttt gattcggtaa tctccgaaca gaaggaagaa cgaaggaagg  300
agcacagact tagattggta tatatacgca tatgtagtgt tgaagaaaca tgaaattgcc  360
cagtattctt aacccaactg cacagaacaa aaacctgcag gaaacgaaga taaatcatgt  420
cgaaagctac atataaggaa cgtgctgcta ctcatcctag tcctgttgct gccaagctat  480
ttaatatcat gcacgaaaag caaacaaact tgtgtgcttc attggatgtt cgtaccacca  540
aggaattact ggagttagtt gaagcattag gtcccaaaat ttgtttacta aaaacacatg  600
tggatatctt gactgatttt tccatggagg cacagttaa accgctaaag gcattatccg   660
ccaagtacaa tttttactc ttcgaagaca gaaaatttgc tgacattggt aatacagtca  720
aattgcagta ctctgcgggt gtatacgaa tagcagaatg ggcagacatt acgaatgcac   780
acggtgtggt gggcccaggt attgttagcg gtttgaagca ggcggcagaa gaagtaacaa  840
aggaacctag aggcctttg atgttagcag aattgtcatg caagggctcc ctatctactg   900
gagaatatac taagggtact gttgacattg cgaagagcga caaagatttt gttatcggct  960
ttattgctca aagagacatg ggtggaagag atgaaggtta cgattggttg attatgacac 1020
ccggtgtggg tttagatgac aagggagcg cattgggtca acagtataga accgtggatg  1080
atgtggtctc tacaggatct gacattatta ttgttggaag aggactattt gcaaagggaa 1140
gggatgctaa ggtagaggt gaacgttaca gaaaagcagg ctgggaagca tatttgagaa 1200
gatgcggcca gcaaaactaa aaaactgtat tataagtaaa tgcatgtata ctaaactcac 1260
aaattagagc ttcaatttaa ttatatcagt tattaccta ttgtgtga aataccgcac 1320
agatgcgtaa ggagaaaata ccgcatcagg aaattgtaaa cgttaatatt ttgttaaaat 1380
tcgcgttaaa ttttttgttaa atcagctcat ttttaacca ataggccgaa atcggcaaaa 1440
tcccttataa atcaaaagaa tagaccgaga tagggttgag tgttgttcca gtttggaaca 1500
agagtccact attaaagaac gtggactcca acgtcaaagg cgcaaaaacc gtctatcagg 1560
gcgatggccc actacgtgaa ccatcacct aatcaagttt tttggggtcg aggtgccgta 1620
aagcactaaa tcggaaccct aaagggagcc cccgatttag agcttgacgg ggaaagccgg 1680
cgaacgtggc gagaaaggaa gggaagaaag cgaaggagc gggcgctagg gcgctggcaa 1740
gtgtagcggt cacgctgcgc gtaaccacca caccgccgc gcttaatgcg ccgctacagg 1800
gcgcgtcgcg ccattcgcca ttcaggctgc gcaactgttg gggaagggcga tcggtgcggg 1860
cctcttcgct attacgccag ctggcgaaag gggatgtgc tgcaaggcga ttaagttggg 1920
taacgccagg gttttcccag tcacgacgtt gtaaaacgac ggccagtgag cgcgcgtaat 1980
acgactcact atagggcgaa ttgggtaccg gccgcaaatt aaagccttcg agcgtcccaa 2040
aaccttctca agcaaggttt tcagtataat gttacatgcg tacacgcgtc tgtacagaaa 2100
aaaaagaaaa atttgaaata taaataacgt tcttaatact aacataacta taaaaaaata 2160
aatagggacc tagacttcag gttgtctaac tccttccttt tcggttagag cggatgtggg 2220
gggagggcgt gaatgtaagc gtgacataac taattacatg actcgaggtc gacggtatcg 2280
ataagcttga tatcgaattc ctgcagcccg gggatccac tagttctttg aaaagataat 2340
gtatgattat gctttcactc atatttatac agaaacttga tgttttcttt cgagtatata 2400
caaggtgatt acatgtacgt ttgaagtaca actctagatt ttgtagtgcc ctcttgggct 2460
agcggtaaag gtgcgcattt tttcacaccc tacaatgttc tgttcaaaag attttggtca 2520
aacgctgtag aagtgaaagt tggtgcgcat gtttcggcgt tcgaaacttc tccgcagtga 2580
aagataaatg atcaacaatg aatatatcta tatgttttag agctagaaat agcaagttaa 2640
aataaggcta gtccgttatc aacttgaaaa agtggcaccg agtcggtggt gcttttttg 2700
tttttatgt cgagctccag ctttttgttcc ctttagtgag ggtaattgc gcgcttggcg 2760
taatcatggt catagctgtt tcctgtgtga aattgttatc cgctcacaat tccacacaa 2820
ataggagccg gaagcataaa gtgtaaagcc tggggtgcct aatgagtgag gtaactcaca 2880
ttaattgcgt tgcgctcact gcccgctttc cagtcgggaa acctgtcgtg ccagctgcat 2940
taatgaatcg gccaacgcgc ggggagaggc ggtttgcgta ttgggcgctc ttccgcttcc 3000
tcgctcactg actcgctgcg ctcggtcgtt cggctgcggc gagcggtatc agctcactca 3060
aaggcggtaa tacggttatc cacagaatca ggggataacg caggaaagaa catgtgagca 3120
aaaggccagc aaaaggccag gaaccgtaaa aaggccgcgt tgctggcgtt tttccatagg 3180
ctccgccccc ctgacgagca tcacaaaaat cgacgctcaa gtcagaggtg gcgaaacccg 3240
acaggactat aaagatacca ggcgtttccc cctggaagct ccctcgtgcg ctctcctgtt 3300
ccgaccctgc cgcttaccgg atacctgtcc gcctttctcc cttcggaag cgtggcgctt 3360
tctcatagct cacgctgtag gtatctcagt tcggtgtagg tcgttcgctc caagctgggc 3420
tgtgtgcacg aaccccccgt tcagcccgac cgctgcgcct tatccggtaa ctatcgtctt 3480
gagtccaacc cggtaagaca cgacttatcg ccactggcag cagccactgg taacaggatt 3540
agcagagcga ggtatgtagg cggtgctaca gagttcttga agtggtggcc taactacggc 3600
tacactagaa ggacagtatt tggtatctgc gctctgctga agccagttac cttcggaaaa 3660
agagttggta gctcttgatc cggcaaacaa accaccgctg gtagcggtgg ttttttttgtt 3720
tgcaagcagc agattacgcg cagaaaaaaa ggatctcaag aagatccttt gatcttttct 3780
acggggtctg acgctcagtg aacgaaaact cacgttaagg gattttggt catgagatta 3840
tcaaaaagga tcttcaccta gatcctttta aattaaaaat gaagttttaa atcaatctaa 3900
agtatatatg agtaaacttg gtctgacagt taccaatgct taatcagtga ggcaccttatc 3960
tcagcgatct gtctatttcg ttcatccata gttgcctgac tccccgtcgt gtagataact 4020
acgatacggg agggcttacc atctggcccc agtgctgcaa tgataccgcg agacccacgc 4080
tcaccggctc cagatttatc agcaataaac cagccagccg aagggccgag cgcagaagt 4140
ggtcctgcaa ctttatccgc ctccatccag tctattaatt gttgccggaa gctagagta 4200
agtagttcgc cagttaatag tttgcgcaac gttgttgcca ttgctacagg catcgtggtg 4260
tcacgctcgt cgtttggtat ggcttcattc agctccggtt cccaacgatc aaggcgagtt 4320
acatgatccc ccatgttgtg caaaaaagcg gttagctcct tcggtcctcc gatcgttgtc 4380
agaagtaagt tggccgcagt gttatcactc atggttatgg cagcactgca taattctctt 4440
actgtcatgc catccgtaag atgcttttct gtgactggtg agtactcaac caagtcattc 4500
```

```
tgagaatagt gtatgcgcg accgagttgc tcttgcccgg cgtcaatacg ggataatacc    4560
gcgccacata gcagaacttt aaaagtgctc atcattggaa aacgttcttc ggggcgaaaa    4620
ctctcaagga tcttaccgct gttgagatcc agttcgatgt aacccactcg tgcacccaac    4680
tgatcttcag catcttttac tttcaccagc gtttctgggt gagcaaaaac aggaaggcaa    4740
aatgccgcaa aaaagggaat aagggccgaca cggaaatgtt gaatactcat actcttcctt    4800
tttcaatatt attgaagcat ttatcagggt tattgtctca tgagcggata catatttgaa    4860
tgtatttaga aaaataaaca aataggggtt ccgcgcacat ttccccgaaa agtgccacct    4920
gaacgaagca tctgtgcttc attttgtaga acaaaaatgc aacgcgagag cgctaatttt    4980
tcaaacaaag aatctgagct gcattttttac agaacagaaa tgcaacgcga aagcgctatt    5040
ttaccaacga agaatctgtg cttcattttt gtaaaacaaa aatgcaacgc gagagcgcta    5100
atttttcaaa caaagaatct gagctgcatt tttacagaac agaaatgcaa cgcgagagcg    5160
ctattttacc aacaaagaat ctatacttct tttttgttct acaaaaatgc atcccgagag    5220
cgctattttt ctaacaaagc atcttagatt actttttttc tcctttgtgc gctctataat    5280
gcagtctctt gataactttt tgcactgtag gtccgttaag gttagaagaa ggctactttg    5340
gtgtctattt tctcttccat aaaaaaaagc tgactccact tcccgcgttt actgattact    5400
agcgaagctg cgggtgcatt ttttcaagat aaaggcatcc ccgattatat tctataccga    5460
tgtggattgc gcatactttg tgaacagaaa gtgatagcgt tgatgattct tcattggtca    5520
gaaaattatg aacggtttct tctatttttgt tctatatac tacgtatagg aaatgtttac    5580
atttttcgtat tgttttcgat tcactctatg aatagttctt actacaattt ttttgtctaa    5640
agagtaaatac tagagataaa cataaaaaat gtagaggtcg agtttagatg caagttcaag    5700
gagcgaaagg tggatgggta ggttatatag ggatatagca cagagatata tagcaaagag    5760
atacttttga gcaatgtttg tggaagcggt attcgcaata tttagtagc tcgttacagt    5820
ccggtgcgtt tttggttttt tgaaagtgcg tcttcagagc gcttttggtt ttcaaaagcg    5880
ctctgaagtt cctatacttt ctagagaata ggaacttcgg aataggaact tcaaagcgtt    5940
tccgaaaacg agcgcttccg aaaatgcaac gcgagctgcg cacatacagc tcactgttca    6000
cgtcgcacct atatctcgt gttgcctgta tatatatata ctagagaaga acggcatagt    6060
gcgtgtttat gcttaaatgc gtacttatat gcgtctattt atgtaggatg aaaggtagtc    6120
tagtacctcc tgtgatatta tcccattcca tgcgggggtat cgtatgcttc cttcagcact    6180
acccttagc tgttctatat gctgccactc tcaattgga ttagtctcat ccttcaatgc    6240
tatcatttcc tttgatattg gatcatacta agaaaccatt attatcatga cattaaccta    6300
taaaaatagg cgtatcacga ggcccttttcg tc                                 6332

SEQ ID NO: 13          moltype = DNA  length = 5858
FEATURE                Location/Qualifiers
misc_feature           1..5858
                       note = Synthetic DNA
source                 1..5858
                       mol_type = other DNA
                       organism = synthetic construct
SEQUENCE: 13
cgccagggtt ttcccagtca cgacgttgta aaacgacggc cagtgaatta gaactcggta     60
cgcgcggatc ttccagagat gtgtccgcgc tgagggttta atggcgcgcc gcggccgccc    120
gcggtgttgg aataaaaatc aactatcatc tactaactag tatttacgtt actagtatat    180
tatcatatac ggtgttagaa gatgacgcaa atgatgagaa atagtcatct aaattagtga    240
aagctgaaac gcaaggattg ataatgtaat aggatcaatg aatattaact tttaaaggtg    300
aactgatcta cgcgccctcg atagtaatga ctaaatatct tgggtagagt atatataatg    360
tcgtattttt gtatattgtt ttatttagac aaatagtaac gtttatgtt ccttcaatcg    420
catctttcat gatctttaat cgatcgtcaa atggatccat ttagagtttc tcatcaccat    480
ccccatatca tttcactcca ccccgcttta cgtaaaaaaa aaaaaaaaaa ttgaataaat    540
gactaagaat tagacacaat tttgtcttaa tgaatgcttt ttacttatga cacatgccag    600
tttgtacata tgttgatctt catagctccg ataatcttca taaattcgtg acaaattaaa    660
attacacatt attatgtaaa ctataatata caatgttgcc tatcaagaca aacatatgca    720
ctctatgatt tgccagctta ctatccttct gaaaatatg cactctatat cttttagttc    780
ttaattgcaa cacatagatt tgctgtataa cgaatttttat gctatttttt aaatttggag    840
ttcagtgata aaagtgtcac agcgaatttc tccacatgta gggaccgaat tgtttacaag    900
ttctctgtac caccatggag acatcaaaaa ttgaaaatct atggaaagat atggacggta    960
gcaacaagaa tatagcacga gccgcggagt tcatttcgtt acttttgata tcactcacaa   1020
ctattgcgaa gcgcttcagt gaaaaaatca taaggaaag ttgtaaatat tattggtagt   1080
attgctttgg taaagtagag ggggtaaaattt tccccttta ttttgttcat acattcttaa   1140
attgctttgc ctctccttt ggaaagctat acttcggagc actgttgagc gaaggctcat   1200
tagatatatt ttctgtcatt ttccttaacc caaaaataag ggaaagggtc caaaagcgc   1260
tcggacaact gttgaccgtg atccgaagga ctggctatac agtgttcaca aaatagccaa   1320
gctgaaaata atgtgtagct atgttcagtt agtttggcta gcaaagatat aaaagcaggt   1380
cggaaatatt tatgggcatt attatgcaga gcatcaacat gataaaaaaa aacagttgaa   1440
tattccctca aaatgggta agggagaaga acttttcact ggagttgtcc caattcttgt   1500
tgaattagat ggtgatgtta atgggcacaa attttctgtc agtggagagg gtgaaggtga   1560
tgcaacatac ggaaaactta cccttaaatt tatttgcact actggaaagc ttcctgttcc   1620
ttggccaaca cttgtcacta ctcttactta tggtgttcaa tgcttttcaa gatacccaga   1680
tcatatgaag cggcacgact tcttcaagag cgccatgcct gagggatacg tgcaggagag   1740
gaccatcttc ttcaaggacg acgggaacta caagacacgt gctgaagtca agtttgaggg   1800
agacaccctc gtcaacagaa tcgagcttaa gggaatcgat ttcaaggagg acggaaacat   1860
cctcggccac aagttggaat acaactacaa ctcccacaac gtatacatca tggcagacaa   1920
acaaaagaat ggaatcaaag ttaacttcaa aattagacac aacattgaag atggaagcgt   1980
tcaactagca gaccattatc aacaaaatac tccaattggc gatggccctg tccttttacc   2040
agacaaccat tacctgtcca cacaatctgc ccttcgaaa gatcccaacg aaaagagaga   2100
ccacatggtc cttcttgagt ttgtaacagc tgctgggatt acacatggca tggatgaact   2160
atacaaataa cactcatacg ccatccttaa agacctggtc tacgatcaaa tgattttttt   2220
agtttacaat ctatttttgt ttctaagcaa gtttatcacg caaatacata agtatatttt   2280
tactttctat tcttcctagt ttatatttat ttcattgtaa ctttctttaga agctcggtcc   2340
```

```
tctcgctata tagtaggatc tgcaacatat ttggatgtgg gtgggcgttc tccttcttt    2400
ttagatgtaa ggtccaacac gtataacagg tgatacacat agaaagacac gtggaaataa    2460
cagtcattta cgaatattta aaacctgagc aactccgtca aatttgatct taatcttttc    2520
tggggcccca tctaattccc agaaagccct tcgaattaga aaccgatgc ttacaaatga    2580
ataacgaaat gagacaaaga agagaaccaa tttttacaag catggggagc gctgattctc    2640
ttttggtacg cttcccatcc agcatttctg tatctttcac cttcaacctt aggatctcta    2700
cccttggcga aaagtcctct gccaacaatg atgatatctg atccaccact acaacttcg    2760
tcgacggttc tgtactgctg acccaatgca tcgcctttgt cgtctaaacc tacacctggg    2820
gtcatgatta gccaatcaaa cccttcttct cttcctccca tatcgttctg agcaatgaac    2880
ccaataacga aatctttatc actctttgca atatcaacgg taccccttagt atattcaccg    2940
tgtgctagag aacccttgga agataattca gcaagcatca ataatcccct tggttctttg    3000
gtgacctctt gcgcaccttg tttcaagcca gcaacaatac cagcaccagt aacccgtgg    3060
gcgttggtga tatcagacca ttctgcgata cggtaaacgc ccgatgtata ttgtaatttg    3120
actgtgttac cgatatcggc gaattttctg tcctcaaata tcaagaactt gtatttctct    3180
gccaatgctt tcaatggaac gacagtaccc tcataactga aatcatccaa gatatcaacg    3240
tgtgttttca aaaggcaaat gtatggaccc aacgtttcaa caagtttcaa tagctcatca    3300
gtcgaacgaa cgtcaagaga agcacacaaa ttggtttttct tttcatccat taaacgtaaa    3360
agtttcgatg caaccggact tgcatgagtc tcagctctac tggtatatga ttttgtggac    3420
atggtgcaac taattgacgg gagtgtattg acgctggcgt actggctttc acaaaatggc    3480
ccaatcacaa ccacatctta gatagttgaa atgacttag ataacatcaa ttgagatgag    3540
cttaatcatg tcaaagctaa aagtgtcacc atgaacgaca attcttaagc aaatcacgtg    3600
atatagatcc acgaataacc accatttgat gctcgaggca agtaatgtgt aaaaaaat    3660
gcgttaccac catccaatgc agaccgatct tctacccaga atcacatata tttatgtacc    3720
gagtaccttt tttctatctt ccaattgctt ctcccatatg attgtctccg taagctcgaa    3780
atttctaagt tggattttaa tcttcacgca ggatgacagt tcgatgagct tctgaggagt    3840
gtttagaaca taatcagttt atccatggtc tatctttct tgtcgctttt tctcctcgat    3900
agaacctaaa taaaaatata aaatgatgat aataatattt atagaattgt gtagaattgc    3960
agattccctt ttatgggattc ctaaatcctg aggagaactt ctagtatatt ctacatacct    4020
aatattattg ccttattaaa aatggaatcc aacaattac atcaaaatcc acattctcag    4080
atctgcggcc gcactcagac ctgaagtgaa gttcctatac atcgtcgaac ggcaggcgtg    4140
caaacttggc gtaatcatgg tcatagctgt ttcctgtgtg aaattgttat ccgcttttcc    4200
ataggctccg ccccccctgac gagcatcaca aaaatcgacg ctcaagtcag aggtggcgaa    4260
acccgacagg actataaaga taccaggcgt ttcccctgg aagctccctc gtgcgctctc    4320
ctgttccgac cctgccgctt accggatacc tgtccgcctt tctccccttcg ggaagcgtgg    4380
cgctttctca tagctccgac tgtaggtatc tcagttcggt gtaggtcgtt cgctccaagc    4440
tgggctgtgt gcacgaaccc cccgttcagc ccgaccgctg cgccttatcc ggtaactatc    4500
gtcttgagtc caaccggta agacacgact tatcgccact ggcagcagcc actggtaaca    4560
ggattagcag agcgaggtat gtaggcggtg ctacagagtt cttgaagtgg tgggctaact    4620
acggctacac tagaagaaca gtatttggta tctgcgctct gctgaagcca gttaccttcg    4680
gaaaaagagt tggtagctct tgatccggca aacaaaccac cgctggtagc ggtggttttt    4740
ttgtttgcaa gcagcagatt acgcgcagaa aaaaaggatc tcaagaagat cctttgatct    4800
ttttctacggg gtctgacgct cagtggaacg acgcgcgcgt aactcacgtt aagggatttt    4860
ggtcatgaga ttgcgccgtc ccgtcaagtc agctaatgc tctgcttacc aatgcttaat    4920
cagtgaggca cctatctcag cgatctgtct atttcgttca tccatagttg cctgactccc    4980
cgtcgtgtag ataactacga tacgggaggg cttaccatct ggccccagcg ctgcgatgat    5040
accgcgagaa ccacgctcac cggctccgga tttatcagca ataaaccagc cagccggaag    5100
ggccgagcgc agaagtggtc ctgcaacttt atccgcctcc atccagtcta ttaattgttg    5160
ccgggaagct agagtaagta gttcgccagt taatagtttg cgcaacgttg ttgccatcgc    5220
tacaggcatc gtggtgtcac gctcgtcgtt tggtatggc tcattcagct ccggttccca    5280
acgatcaagg cgagttacat gatccccat gttgtgcaaa aaagcggtta gctccttcgg    5340
tcctccgatc gttgtcagaa gtaagttggc cgcagtgtta tcactcatgg ttatgcagac    5400
actgcataat tctcttactg tcatgccatc cgtaagatgc ttttctgtga ctggtgagta    5460
ctcaaccaag tcattctgag aatagtgtat gcggcgaccg agttgctctt gcccggcgtc    5520
aatacgggat aataccgcgc cacatagcag aactttaaaa gtgctcatca ttggaaaacg    5580
ttcttcgggg cgaaaactct caaggatctt accgctgttg agatccagtt cgatgtaacc    5640
cactcgtgca cccaactgat cttcagcatc ttttactttc accagcgttt ctgggtgagc    5700
aaaaacagga aggcaaaatg ccgcaaaaaa gggaataagg gcgacacgga aatgttgaat    5760
actcatattc ttccttttc aatattattg aagcatttat cagggttatt gtctcatgag    5820
cggatacata tttgaatgta tttagaaaaa taaacaaa                              5858

SEQ ID NO: 14          moltype = AA  length = 344
FEATURE                Location/Qualifiers
source                 1..344
                       mol_type = protein
                       organism = Aspergillus nidulans
SEQUENCE: 14
MVQDTSSAST SPILTRWYID TRPLTASTAA LPLLETLQPA DQISVQKYYH LKDKHMSLAS    60
NLLKYLFVHR NCRIPWSSIV ISRTPDPHRR PCYIPPSGSQ EDSFKDGYTG INVEFNVSHQ   120
ASMVAIAGTA FTPNSGGDSK LKPEVGIDIT CVNERQGRNG EERSLESLRQ YIDIFSEVFS   180
TAEMANIRRL DGVSSSSLSA DRLVDYGYRL FYTYWALKEA YIKMTGEALL APWLRELEFS   240
NVVAPAAVAE SGDSAGDFGE PYTGVRTTLY KNLVEDVRIE VAALGGDYLF ATAARGGGIG   300
ASSRPGGGPD GSGIRSQDPW RPFKKLDIER DIQPCATGVC NCLS                    344

SEQ ID NO: 15          moltype = AA  length = 403
FEATURE                Location/Qualifiers
source                 1..403
                       mol_type = protein
                       organism = Aloe arborescens
SEQUENCE: 15
```

```
MSSLSNASHL MEDVQGIRKA QRADGTATVM AIGTAHPPHI FPQDTYADFY FRATNSEHKV    60
ELKKKFDRIC KKTMIGKRYF NYDEEFLKKY PNITSFDEPS LNDRQDICVP GVPALGAEAA   120
VKAIAEWGRP KSEITHLVFC TSCGVDMPSA DFQCAKLLGL RTNVNKYCVY MQGCYAGGTV   180
MRYAKDLAEN NRGARVLVVC AELTIIGLRG PNESHLDNAI GNSLFGDGAA ALIVGSDPII   240
GVEKPMFEIV CAKQTVIPNS EDVIHLHMRE AGLMFYMSKD SPETISNNVE ACLVDVFKSV   300
GMTPPEDWNS LFWIPHPGGR AILDQVEAKL KLRPEKFRAT RTVLWDCGNM VSACVLYILD   360
EMRRKSADEG LETYGEGLEW GVLLGFGPGM TVETILLHSL PLM                     403

SEQ ID NO: 16           moltype = AA   length = 169
FEATURE                 Location/Qualifiers
source                  1..169
                        mol_type = protein
                        organism = Streptomyces sp.
SEQUENCE: 16
MRHVEHTVTV AAPADLVWEV LADVLGYADI FPPTEKVEIL EEGQGYQVVR LHVDVAGEIN    60
TWTSRRDLDP ARRVIAYRQL ETAPIVGHMS GEWRAFTLDA ERTQLVLTHD FVTRAAGDDG   120
LVAGKLTPDE AREMLEAVVE RNSVADLNAV LGEAERRVRA AGGVGTVTA               169

SEQ ID NO: 17           moltype = AA   length = 256
FEATURE                 Location/Qualifiers
source                  1..256
                        mol_type = protein
                        organism = Streptomyces sp.
SEQUENCE: 17
MSGRKTFLDL SFATRDTPSE ATPVVVDLLD HVTGATVLGL SPEDFPDGMA ISNETVTLTT    60
HTGTHMDAPL HYGPLSGGVP AKSIDQVPLE WCYGPGVRLD VRHVPAGDGI TVDHLNAALD   120
AAEHDLAPGD IVMLWTGADA LWGTREYLST FPGLTGKGTQ FLVEAGVKVI GIDAWGLDRP   180
MAAMIEEYRR TGDKGALWPA HVYGRTREYL QLEKLNNLGA LPGATGYDIS CFPVAVAGTG   240
AGWTRVVAVF EQEEED                                                   256

SEQ ID NO: 18           moltype = AA   length = 515
FEATURE                 Location/Qualifiers
source                  1..515
                        mol_type = protein
                        organism = Dactylopius coccu
SEQUENCE: 18
MEFRLLILAL FSVLMSTSNG AEILALFPIH GISNYNVAEA LLKTLANRGH NVTVVTSFPQ    60
KKPVPNLYEI DVSGAKGLAT NSIHFERLQT IIQDVKSNFK NMVRLSRTYC EIMFSDPRVL   120
NIRDKKFDLV INAVFGSDCD AGFAWKSQAP LISILNARHT PWALHRMGNP SNPAYMPVIH   180
SRFPVKMNFF QRMINTGWHL YFLYMYFYYG NGEDANKMAR KFFGNDMPDI NEMVFNTSLL   240
FVNTHFSVDM PYPLVPNCIE IGGIHVKEPQ PLPLEIQKFM DEAEHGVIFF TLGSMVRTST   300
FPNQTIQAFK EAFAELPQRV LWKFENENED MPSNVLIRKW FPQNDIFGHK NIKAFISHGG   360
NSGALEAVHF GVPIIGIPLF YDQYRNILSF VKEGVAVLLD VNDLTKDNIL SSVRTVVNDK   420
SYSERMKALS QLFRDRPMSP LDTAVYWTEY VIRHRGAHHL KTAGAFLHWY QYLLLDVITF   480
LLVTFCAFCF IVKYICKALI HHYWSSSKSE KLKKN                              515

SEQ ID NO: 19           moltype = AA   length = 417
FEATURE                 Location/Qualifiers
source                  1..417
                        mol_type = protein
                        organism = Aspergillus nidulans
SEQUENCE: 19
MTLPVLIIGA GLSGLTTARL LTNAHIPCIV FEASPPSRTQ GYAISLRDWG FNALLRALGN    60
LPLSSLTRAV APDRHIGGWG WLDQSWRNNQ TGEIIMMPPK ESKEKPTILR ANRNALRQWI   120
ADAGVGEDEE IDVRYGHRLV GVQLLREGGD GNVVTAEFAN GATYTGSLLI AADGVHSTVR   180
TLILPAVKPE ILPVLVYHGD FKLSREEYEC VIRPHAGEST IVAGVGDGFN TPLTVCDVTS   240
TTVHMDWTYS RPSIGDNDPL YNPNITSEEA KVIPEALIEE INAKKLGEPW SLFLNGEAMR   300
RHRVFNWLTR CVSMERSDVN SCTGKGVVFV GDSWHAMPIF GGEGGNHAIF DGIELAKMLE   360
VAWGRSKEDV QAAIGKYYDK SWRRCNDAVR RSKQRFYQLH RPISEWIEIA EKQKMRA      417

SEQ ID NO: 20           moltype = DNA   length = 852
FEATURE                 Location/Qualifiers
source                  1..852
                        mol_type = genomic DNA
                        organism = Saccharomyces cerevisiae
SEQUENCE: 20
atgtctgaca aggaacaaac gagcggaaac acagatttgg agaatgcacc agcaggatac    60
tatagttccc atgataacga cgttaatggc gttgcagaag atgaacgtcc atctcatgat   120
tcgttgggca agatttacac tggaggtgat aacaatgaat atatctatat tgggcgtcaa   180
aagtttttga agagcgactt ataccaagcc tttgtggta ccttgaatcc agggttagct    240
cctgctccag tgcacaaatt tgctaatcct gcgcccttag tctttcagc cttcgcgttg    300
acgacatttg tgctgtccat gttcaatgcg agagcgcaag gatcactgt tcctaatgtt    360
gtcgtcggtt gtgctatgtt ttatggtggt ttggtgcaat tgattgctgg tatttgggag   420
atggcttgg aaaatacttt tggtggtacc gcattatgtt cttacggtgg gtttttgtta   480
agtttcgctg caatttacat tccttggttt ggtatcttgg aagcttacga agacaatgaa   540
tctgatttga ataatgcttt aggattttat ttgttgggg gggccatctt tacgtttggt   600
ttaaccgttt gtaccatgaa atccactgtt atgttctttt tgttgttctt cttactgcag    660
ttaactttcc tactgttgtc tattggtcac tttgctaata gacttggtgt cacaagagct   720
ggtggtgtcc tgggagttgt tgttgctttc attgcttggt acaacgcata tgcaggtgtt   780
```

```
gctacaaagc agaattcata tgtactggct cgtccattcc cattaccatc tactgaaagg    840
gtaatctttt aa                                                        852

SEQ ID NO: 21           moltype = DNA   length = 1308
FEATURE                 Location/Qualifiers
source                  1..1308
                        mol_type = genomic DNA
                        organism = Saccharomyces cerevisiae
SEQUENCE: 21
atggactaca acaagagatc ttcggtctca accgtgccta atgcagctcc cataagagtc     60
ggattcgtcg gtctcaacgc agccaaagga tgggcaatca agacacatta ccccgccata    120
ctgcaactat cgtcacaatt tcaaatcact gccttataca gtccaaaaat tgagacttct    180
attgccacca ttcagcgtct aaaattgagt aatgccactg cttttcccac tttagagtca    240
tttgcatcat cttccactat agatatgata gtgatagcta tccaagtggc cagccattat    300
gaagttgtta tgcctctctt ggaattctcc aaaaataatc cgaacctcaa gtatcttttc    360
gtagaatggg cccttgcatg ttcactagat caagccgaat ccattatcaa ggctgctgct    420
gaacgtgggg ttcaaaccat catctcttta caaggtcgta atcaccata tattttgaga     480
gcaaaagaat taatatctca aggctatatc ggcgacatta atcgatcga gattgctgga    540
aatggcggtt ggtacggcta cgaaaggcct gttaaatcac caaaatacat ctatgaaatc    600
gggaacggtg tagatctggt aaccacaaca tttggtcaca caatcgatat tttacaatac    660
atgacaagtt cgtactttc caggataaat gcaatggttt tcaataatat tccagagcaa    720
gagctgatag atgagcgtgg taaccgattg ggccagcgaa tcccaaagac agtaccggat    780
catcttttat tccaaggcac attgttaaat ggcaatgttc cagtgtcatg cagttttcaaa   840
ggtggcaaac ctaccaaaaa aatttggtca ttgacattca cggtaccaag                900
ggagatttga aacttgaagg cgatgccggc ttcgcagaaa tttcaaatct ggtccttac    960
tacagtggaa ctagagcaaa cgacttcccg ctagccaagc gacaacaagc tcctttagac    1020
ccggggtatg atgcaggtaa agaaatcatg gaagtatatc atttacgaaa ttataatgcc    1080
attgtgggta atattcatcg actgtatcaa tctatctctg acttccactt caatacaaag    1140
aaaattcctg aattaccctc acaatttgta atgcaaggtt tcgatttcga aggctttccc    1200
accttgatgg atgctctgat attacacagg ttaatcgaga gcgtttataa aagtaacatg    1260
atgggctcca cattaaacgt tagcaatatc tcgcattata gtttataa                 1308

SEQ ID NO: 22           moltype = DNA   length = 852
FEATURE                 Location/Qualifiers
source                  1..852
                        mol_type = genomic DNA
                        organism = Saccharomyces cerevisiae
SEQUENCE: 22
atgtctgaca aggaacaaac gagcggaaac acagatttgg agaatgcacc agcaggatac     60
tatagttccc atgataacga cgttaatggc gttgcagaag atgaacgtcc atctcatgat    120
tcgttgggca agatttacac tggaggtgat aacaatgaat atatctatat tgggcgtcaa    180
aagttttga gagcgactt ataccaagcc tttggtggta ccttgaatcc agggttagct     240
cctgctccag tgcacaaatt tgctaatcct gcgcccttac gtcttcaag cttcgcgttg    300
acgacatttg tgctgtccat gttcaatgcg agagcgcaag ggatcactgt tcctaatgtt    360
gtcgtcggtt gtgctatgtt ttatggtggt ttggtgcaat tgattgctgg tatttgggag    420
atagctttg aaaaatactt tggtggtacc gcattatgtt cttacggtgg gttttggttg     480
agtttcgctg caatttacat tccttggttt ggtatcttgg aagcttacga agacaatgaa    540
tctgatttga ataatgcttt aggattttat ttgttggggt gggccatctt acgtttggt     600
ttaaccgttt gtaccatgaa atccactgtt atgttctttt tgttgttctt cttactagca    660
ttaactttcc tactgttgtc tattggtcac tttgctaata gacttggtgt cacaagagct    720
ggtggtgtcc tgggagttgt tgttgctttc attgcttggt acaacgcata tgcaggtgtt    780
gctacaaagc agaattcata tgtactggct cgtccattcc cattaccatc tactgaaagg    840
gtaatctttt aa                                                        852

SEQ ID NO: 23           moltype = DNA   length = 42
FEATURE                 Location/Qualifiers
misc_feature            1..42
                        note = Synthetic DNA
source                  1..42
                        mol_type = other DNA
                        organism = synthetic construct
SEQUENCE: 23
gcgaagaatt ttaagcagta acagtaccaa caccaccagc ag                         42

SEQ ID NO: 24           moltype = DNA   length = 41
FEATURE                 Location/Qualifiers
misc_feature            1..41
                        note = Synthetic DNA
source                  1..41
                        mol_type = other DNA
                        organism = synthetic construct
SEQUENCE: 24
tctagaacta atgagacatg ttgaacatac tgttactgtc g                          41

SEQ ID NO: 25           moltype = DNA   length = 52
FEATURE                 Location/Qualifiers
misc_feature            1..52
                        note = Synthetic DNA
source                  1..52
```

```
                        mol_type = other DNA
                        organism = synthetic construct
SEQUENCE: 25
catgtctcat tagttctaga aaacttagat tagattgcta tgctttcttt ct        52

SEQ ID NO: 26           moltype = DNA  length = 35
FEATURE                 Location/Qualifiers
misc_feature            1..35
                        note = Synthetic DNA
source                  1..35
                        mol_type = other DNA
                        organism = synthetic construct
SEQUENCE: 26
tactgcttaa aattcttcgc cagaggtttg gtcaa                           35

SEQ ID NO: 27           moltype = DNA  length = 41
FEATURE                 Location/Qualifiers
misc_feature            1..41
                        note = Synthetic DNA
source                  1..41
                        mol_type = other DNA
                        organism = synthetic construct
SEQUENCE: 27
ttcgacggat atgtctggta gaaagacttt cttggatttg t                    41

SEQ ID NO: 28           moltype = DNA  length = 46
FEATURE                 Location/Qualifiers
misc_feature            1..46
                        note = Synthetic DNA
source                  1..46
                        mol_type = other DNA
                        organism = synthetic construct
SEQUENCE: 28
gtgacataac ttaatcttct tcttcttgtt cgaaaacagc aacaac               46

SEQ ID NO: 29           moltype = DNA  length = 35
FEATURE                 Location/Qualifiers
misc_feature            1..35
                        note = Synthetic DNA
source                  1..35
                        mol_type = other DNA
                        organism = synthetic construct
SEQUENCE: 29
agaagattaa gttatgtcac gcttacattc acgcc                           35

SEQ ID NO: 30           moltype = DNA  length = 35
FEATURE                 Location/Qualifiers
misc_feature            1..35
                        note = Synthetic DNA
source                  1..35
                        mol_type = other DNA
                        organism = synthetic construct
SEQUENCE: 30
taccagacat atccgtcgaa actaagttct ggtgt                           35

SEQ ID NO: 31           moltype = DNA  length = 46
FEATURE                 Location/Qualifiers
misc_feature            1..46
                        note = Synthetic DNA
source                  1..46
                        mol_type = other DNA
                        organism = synthetic construct
SEQUENCE: 31
tcaattcaat ttacatcaat ggcaaagaat gcaacaaaat agtttc               46

SEQ ID NO: 32           moltype = DNA  length = 34
FEATURE                 Location/Qualifiers
misc_feature            1..34
                        note = Synthetic DNA
source                  1..34
                        mol_type = other DNA
                        organism = synthetic construct
SEQUENCE: 32
aagaagtaac atgtcctctt tgtccaacgc ttcc                            34

SEQ ID NO: 33           moltype = DNA  length = 48
FEATURE                 Location/Qualifiers
misc_feature            1..48
                        note = Synthetic DNA
```

```
                        source                  1..48
                                                mol_type = other DNA
                                                organism = synthetic construct
                        SEQUENCE: 33
                        aagaggacat gttacttctt tttcactgga aaaaaaggg aatgaaac              48

SEQ ID NO: 34           moltype = DNA  length = 29
                        FEATURE                 Location/Qualifiers
                        misc_feature            1..29
                                                note = Synthetic DNA
                        source                  1..29
                                                mol_type = other DNA
                                                organism = synthetic construct
                        SEQUENCE: 34
                        ttcgacgatt gaagacgatg aggccggtg                                  29

SEQ ID NO: 35           moltype = DNA  length = 51
                        FEATURE                 Location/Qualifiers
                        misc_feature            1..51
                                                note = Synthetic DNA
                        source                  1..51
                                                mol_type = other DNA
                                                organism = synthetic construct
                        SEQUENCE: 35
                        tccagagatt tttgaacctc attgtatttt acgaaaaga atatcatact c          51

SEQ ID NO: 36           moltype = DNA  length = 58
                        FEATURE                 Location/Qualifiers
                        misc_feature            1..58
                                                note = Synthetic DNA
                        source                  1..58
                                                mol_type = other DNA
                                                organism = synthetic construct
                        SEQUENCE: 36
                        attgatgtaa attgaattga attgaaatcg atagatcaat ttttttcttt tctctttc   58

SEQ ID NO: 37           moltype = DNA  length = 28
                        FEATURE                 Location/Qualifiers
                        misc_feature            1..28
                                                note = Synthetic DNA
                        source                  1..28
                                                mol_type = other DNA
                                                organism = synthetic construct
                        SEQUENCE: 37
                        catcgtcttc aatcgtcgaa cggcaggc                                   28

SEQ ID NO: 38           moltype = DNA  length = 30
                        FEATURE                 Location/Qualifiers
                        misc_feature            1..30
                                                note = Synthetic DNA
                        source                  1..30
                                                mol_type = other DNA
                                                organism = synthetic construct
                        SEQUENCE: 38
                        gaggttcaaa aatctctgga agatccgcgc                                 30

SEQ ID NO: 39           moltype = DNA  length = 47
                        FEATURE                 Location/Qualifiers
                        misc_feature            1..47
                                                note = Synthetic DNA
                        source                  1..47
                                                mol_type = other DNA
                                                organism = synthetic construct
                        SEQUENCE: 39
                        acaaaacaaa atggaattca gattattgat tttggcttta ttctctg              47

SEQ ID NO: 40           moltype = DNA  length = 48
                        FEATURE                 Location/Qualifiers
                        misc_feature            1..48
                                                note = Synthetic DNA
                        source                  1..48
                                                mol_type = other DNA
                                                organism = synthetic construct
                        SEQUENCE: 40
                        agctggcaaa ttagttcttc ttcaactttt cagacttaga agaagacc             48

SEQ ID NO: 41           moltype = DNA  length = 28
                        FEATURE                 Location/Qualifiers
                        misc_feature            1..28
```

```
                    note = Synthetic DNA
source              1..28
                    mol_type = other DNA
                    organism = synthetic construct
SEQUENCE: 41
tccagagatt gaaaccacac cgtggggc                                          28

SEQ ID NO: 42           moltype = DNA   length = 51
FEATURE                 Location/Qualifiers
misc_feature            1..51
                        note = Synthetic DNA
source                  1..51
                        mol_type = other DNA
                        organism = synthetic construct
SEQUENCE: 42
tgaattccat tttgttttgt gtgtaaattt agtgaagtac tgttttttgt g                51

SEQ ID NO: 43           moltype = DNA   length = 43
FEATURE                 Location/Qualifiers
misc_feature            1..43
                        note = Synthetic DNA
source                  1..43
                        mol_type = other DNA
                        organism = synthetic construct
SEQUENCE: 43
gaagaactaa tttgccagct tactatcctt cttgaaaata tgc                         43

SEQ ID NO: 44           moltype = DNA   length = 52
FEATURE                 Location/Qualifiers
misc_feature            1..52
                        note = Synthetic DNA
source                  1..52
                        mol_type = other DNA
                        organism = synthetic construct
SEQUENCE: 44
ttcgacgatt ttttgaggga atattcaact gttttttttt atcatgttga tg               52

SEQ ID NO: 45           moltype = DNA   length = 28
FEATURE                 Location/Qualifiers
misc_feature            1..28
                        note = Synthetic DNA
source                  1..28
                        mol_type = other DNA
                        organism = synthetic construct
SEQUENCE: 45
tccctcaaaa aatcgtcgaa cggcaggc                                          28

SEQ ID NO: 46           moltype = DNA   length = 30
FEATURE                 Location/Qualifiers
misc_feature            1..30
                        note = Synthetic DNA
source                  1..30
                        mol_type = other DNA
                        organism = synthetic construct
SEQUENCE: 46
gtgtggtttc aatctctgga agatccgcgc                                        30

SEQ ID NO: 47           moltype = DNA   length = 38
FEATURE                 Location/Qualifiers
misc_feature            1..38
                        note = Synthetic DNA
source                  1..38
                        mol_type = other DNA
                        organism = synthetic construct
SEQUENCE: 47
tccagagatt atgactttgc cagttttgat tattggtg                               38

SEQ ID NO: 48           moltype = DNA   length = 39
FEATURE                 Location/Qualifiers
misc_feature            1..39
                        note = Synthetic DNA
source                  1..39
                        mol_type = other DNA
                        organism = synthetic construct
SEQUENCE: 48
tcatatgtga ttaagctctc atcttttgct tttcagcga                              39

SEQ ID NO: 49           moltype = DNA   length = 44
FEATURE                 Location/Qualifiers
```

```
misc_feature            1..44
                        note = Synthetic DNA
source                  1..44
                        mol_type = other DNA
                        organism = synthetic construct
SEQUENCE: 49
gagagcttaa tcacatatga aagtatatac ccgcttttgt acac                   44

SEQ ID NO: 50           moltype = DNA  length = 49
FEATURE                 Location/Qualifiers
misc_feature            1..49
                        note = Synthetic DNA
source                  1..49
                        mol_type = other DNA
                        organism = synthetic construct
SEQUENCE: 50
ttcgacgatt gagagtagac tttttctgtg aaatttaatg agttttttgt             49

SEQ ID NO: 51           moltype = DNA  length = 28
FEATURE                 Location/Qualifiers
misc_feature            1..28
                        note = Synthetic DNA
source                  1..28
                        mol_type = other DNA
                        organism = synthetic construct
SEQUENCE: 51
gtctactctc aatcgtcgaa cggcaggc                                     28

SEQ ID NO: 52           moltype = DNA  length = 30
FEATURE                 Location/Qualifiers
misc_feature            1..30
                        note = Synthetic DNA
source                  1..30
                        mol_type = other DNA
                        organism = synthetic construct
SEQUENCE: 52
gcaaagtcat aatctctgga agatccgcgc                                   30

SEQ ID NO: 53           moltype = DNA  length = 42
FEATURE                 Location/Qualifiers
misc_feature            1..42
                        note = Synthetic DNA
source                  1..42
                        mol_type = other DNA
                        organism = synthetic construct
SEQUENCE: 53
aaaaactata atggttcaag atacttcttc agcttctaca tc                     42

SEQ ID NO: 54           moltype = DNA  length = 46
FEATURE                 Location/Qualifiers
misc_feature            1..46
                        note = Synthetic DNA
source                  1..46
                        mol_type = other DNA
                        organism = synthetic construct
SEQUENCE: 54
aattacatga ttaagataaa caattacaaa cacctgtagc acatgg                 46

SEQ ID NO: 55           moltype = DNA  length = 55
FEATURE                 Location/Qualifiers
misc_feature            1..55
                        note = Synthetic DNA
source                  1..55
                        mol_type = other DNA
                        organism = synthetic construct
SEQUENCE: 55
taactgatca ttatattgaa ttttcaaaaa ttcttacttt tttttttggat ggacg      55

SEQ ID NO: 56           moltype = DNA  length = 57
FEATURE                 Location/Qualifiers
misc_feature            1..57
                        note = Synthetic DNA
source                  1..57
                        mol_type = other DNA
                        organism = synthetic construct
SEQUENCE: 56
cttgaaccat tatagttttt tctccttgac gttaaagtat agaggtatat taacaat     57

SEQ ID NO: 57           moltype = DNA  length = 44
```

```
FEATURE                 Location/Qualifiers
misc_feature            1..44
                        note = Synthetic DNA
source                  1..44
                        mol_type = other DNA
                        organism = synthetic construct
SEQUENCE: 57
tttatcttaa tcatgtaatt agttatgtca cgcttacatt cacg             44

SEQ ID NO: 58           moltype = DNA  length = 32
FEATURE                 Location/Qualifiers
misc_feature            1..32
                        note = Synthetic DNA
source                  1..32
                        mol_type = other DNA
                        organism = synthetic construct
SEQUENCE: 58
ttcaatataa tgatcagtta actccggacc gc                          32

SEQ ID NO: 59           moltype = DNA  length = 51
FEATURE                 Location/Qualifiers
misc_feature            1..51
                        note = Synthetic DNA
source                  1..51
                        mol_type = other DNA
                        organism = synthetic construct
SEQUENCE: 59
gtcgtattac tttgaacctc attgtatttt acggaaaaga atatcatact c     51

SEQ ID NO: 60           moltype = DNA  length = 34
FEATURE                 Location/Qualifiers
misc_feature            1..34
                        note = Synthetic DNA
source                  1..34
                        mol_type = other DNA
                        organism = synthetic construct
SEQUENCE: 60
gtgtggtttc gaggcttgtc agtacatcag cgat                        34

SEQ ID NO: 61           moltype = DNA  length = 28
FEATURE                 Location/Qualifiers
misc_feature            1..28
                        note = Synthetic DNA
source                  1..28
                        mol_type = other DNA
                        organism = synthetic construct
SEQUENCE: 61
gacaagcctc gaaaccacac cgtggggc                               28

SEQ ID NO: 62           moltype = DNA  length = 52
FEATURE                 Location/Qualifiers
misc_feature            1..52
                        note = Synthetic DNA
source                  1..52
                        mol_type = other DNA
                        organism = synthetic construct
SEQUENCE: 62
gtgagcgcgc ttttgaggga atattcaact gttttttttt atcatgttga tg    52

SEQ ID NO: 63           moltype = DNA  length = 25
FEATURE                 Location/Qualifiers
misc_feature            1..25
                        note = Synthetic DNA
source                  1..25
                        mol_type = other DNA
                        organism = synthetic construct
SEQUENCE: 63
tccctcaaaa gcgcgctcac tggcc                                  25

SEQ ID NO: 64           moltype = DNA  length = 39
FEATURE                 Location/Qualifiers
misc_feature            1..39
                        note = Synthetic DNA
source                  1..39
                        mol_type = other DNA
                        organism = synthetic construct
SEQUENCE: 64
gaggttcaaa gtaatacgac tcactatagg gcgaattgg                   39
```

| SEQ ID NO: 65 | moltype = DNA  length = 38 |
| --- | --- |
| FEATURE | Location/Qualifiers |
| misc_feature | 1..38 |
| | note = Synthetic DNA |
| source | 1..38 |
| | mol_type = other DNA |
| | organism = synthetic construct |

SEQUENCE: 65
tccctcaaaa atgactttgc cagttttgat tattggtg                               38

| SEQ ID NO: 66 | moltype = DNA  length = 51 |
| --- | --- |
| FEATURE | Location/Qualifiers |
| misc_feature | 1..51 |
| | note = Synthetic DNA |
| source | 1..51 |
| | mol_type = other DNA |
| | organism = synthetic construct |

SEQUENCE: 66
gtgagcgcgc gagagtagac tttttctgtg aaatttaatg agttttttgtt c               51

| SEQ ID NO: 67 | moltype = DNA  length = 25 |
| --- | --- |
| FEATURE | Location/Qualifiers |
| misc_feature | 1..25 |
| | note = Synthetic DNA |
| source | 1..25 |
| | mol_type = other DNA |
| | organism = synthetic construct |

SEQUENCE: 67
gtctactctc gcgcgctcac tggcc                                             25

| SEQ ID NO: 68 | moltype = DNA  length = 49 |
| --- | --- |
| FEATURE | Location/Qualifiers |
| misc_feature | 1..49 |
| | note = Synthetic DNA |
| source | 1..49 |
| | mol_type = other DNA |
| | organism = synthetic construct |

SEQUENCE: 68
gcaaagtcat ttttgaggga atattcaact gttttttttt atcatgttg                   49

| SEQ ID NO: 69 | moltype = DNA  length = 43 |
| --- | --- |
| FEATURE | Location/Qualifiers |
| misc_feature | 1..43 |
| | note = Synthetic DNA |
| source | 1..43 |
| | mol_type = other DNA |
| | organism = synthetic construct |

SEQUENCE: 69
tcatgtttat ggtagaacta gagaatactt gcaattagaa aag                         43

| SEQ ID NO: 70 | moltype = DNA  length = 27 |
| --- | --- |
| FEATURE | Location/Qualifiers |
| misc_feature | 1..27 |
| | note = Synthetic DNA |
| source | 1..27 |
| | mol_type = other DNA |
| | organism = synthetic construct |

SEQUENCE: 70
gttttgtggg attgtggtaa catggtc                                           27

| SEQ ID NO: 71 | moltype = DNA  length = 99 |
| --- | --- |
| FEATURE | Location/Qualifiers |
| misc_feature | 1..99 |
| | note = Synthetic DNA |
| source | 1..99 |
| | mol_type = other DNA |
| | organism = synthetic construct |

SEQUENCE: 71
atgtctgaca aggaacaaac gagcggaaac acagatttgg agaatgcacc agcaggatac       60
ttatattgaa ttttcaaaaa ttcttacttt tttttttgga                             99

| SEQ ID NO: 72 | moltype = DNA  length = 87 |
| --- | --- |
| FEATURE | Location/Qualifiers |
| misc_feature | 1..87 |
| | note = Synthetic DNA |
| source | 1..87 |
| | mol_type = other DNA |
| | organism = synthetic construct |

SEQUENCE: 72

```
catagcacaa ccgacgacaa cattaggaac agtgatccct tgcgctctcg cattgaacgt    60
aatacgactc actatagggc gaattgg                                        87

SEQ ID NO: 73            moltype = DNA  length = 20
FEATURE                  Location/Qualifiers
misc_feature             1..20
                         note = Synthetic DNA
source                   1..20
                         mol_type = other DNA
                         organism = synthetic construct
SEQUENCE: 73
gctactgctg caagaggtgg                                                20

SEQ ID NO: 74            moltype = DNA  length = 27
FEATURE                  Location/Qualifiers
misc_feature             1..27
                         note = Synthetic DNA
source                   1..27
                         mol_type = other DNA
                         organism = synthetic construct
SEQUENCE: 74
catggtacaa acggttaaac caaacgt                                        27

SEQ ID NO: 75            moltype = DNA  length = 43
FEATURE                  Location/Qualifiers
misc_feature             1..43
                         note = Synthetic DNA
source                   1..43
                         mol_type = other DNA
                         organism = synthetic construct
SEQUENCE: 75
tcatgtttat ggtagaacta gagaatactt gcaattagaa aag                      43

SEQ ID NO: 76            moltype = DNA  length = 27
FEATURE                  Location/Qualifiers
misc_feature             1..27
                         note = Synthetic DNA
source                   1..27
                         mol_type = other DNA
                         organism = synthetic construct
SEQUENCE: 76
gttttgtggg attgtggtaa catggtc                                        27

SEQ ID NO: 77            moltype = DNA  length = 52
FEATURE                  Location/Qualifiers
misc_feature             1..52
                         note = Synthetic DNA
source                   1..52
                         mol_type = other DNA
                         organism = synthetic construct
SEQUENCE: 77
aaaaagtcta ctctcttaca aatgaataac gaaatgagac aaagaagaga ac            52

SEQ ID NO: 78            moltype = DNA  length = 60
FEATURE                  Location/Qualifiers
misc_feature             1..60
                         note = Synthetic DNA
source                   1..60
                         mol_type = other DNA
                         organism = synthetic construct
SEQUENCE: 78
agctggcgta atagcgttaa tattcattga tcctattaca ttatcaatcc ttgcgtttca    60

SEQ ID NO: 79            moltype = DNA  length = 40
FEATURE                  Location/Qualifiers
misc_feature             1..40
                         note = Synthetic DNA
source                   1..40
                         mol_type = other DNA
                         organism = synthetic construct
SEQUENCE: 79
tcaatgaata ttaacgctat tacgccagct gaattggagc                          40

SEQ ID NO: 80            moltype = DNA  length = 58
FEATURE                  Location/Qualifiers
misc_feature             1..58
                         note = Synthetic DNA
source                   1..58
                         mol_type = other DNA
```

-continued

```
                        organism = synthetic construct
SEQUENCE: 80
gttattcatt tgtaagagag tagacttttt ctgtgaaatt taatgagttt ttgttcac      58

SEQ ID NO: 81           moltype = DNA  length = 87
FEATURE                 Location/Qualifiers
misc_feature            1..87
                        note = Synthetic DNA
source                  1..87
                        mol_type = other DNA
                        organism = synthetic construct
SEQUENCE: 81
gtgtccgcgc tgagggttta atggcgcgcc gcggccgccc gcggtgttgg aataaaaatc   60
aactatcatc tactaactag tatttac                                        87

SEQ ID NO: 82           moltype = DNA  length = 89
FEATURE                 Location/Qualifiers
misc_feature            1..89
                        note = Synthetic DNA
source                  1..89
                        mol_type = other DNA
                        organism = synthetic construct
SEQUENCE: 82
gtataggaac ttcacttcag gtctgagtgc ggccgcagat ctgagaatgt ggattttgat   60
gtaattgttg ggattccatt tttaataag                                      89
```

CONSTRUCTION OF RECOMBINANT SACCHAROMYCES CEREVISIAE FOR SYNTHESIZING CARMINIC ACID AND APPLICATION THEREOF

TECHNICAL FIELD

The disclosure relates to construction of recombinant *Saccharomyces cerevisiae* for synthesizing carminic acid and an application thereof, and belongs to the technical field of genetic engineering and bioengineering.

BACKGROUND

Pigments derived from insects, particularly, scale insects, have been used by human beings since ancient times for dyeing textile, in cosmetics and in paints and for coloring foods. The most commonly used scale insect dyes include Kermesic acid, Laccaic acids and Carminic acid, which share a red color hue due to a similar chromophore structure. These compounds have been reported to be produced by five distantly related scale insects (hemiptera), namely *Porphyrophora hamelii* (Armenian/Ararat cochineal), Kermes vermilio, *Porphyrophora polonica* (Polish nematode), *Dactylopius coccus* (Mexican cochineal) and Kerria lacca (Indian lac insect). These insects have at various points in history, and at different geographical localities, been utilized by humans for large scale production of coccid dyes. Carminic acid and its aluminum salt carmine (E120) is by many considered as the pinnacle of coccid dyes, based on its hue, light, temperature, and oxidation stability, and the yields by which it can be obtained from natural sources, for example, *P. hamelii* (Asia), *P. polonica* (Europe) and *D. coccus* (Central America and South America). Therefore, present day production of carminic acid is based on *D. coccus* due to its exceptional high pigment content (16-22% of dry weight), low fat content, and the ease by which the insect can be cultured and harvested from leaves of *Opuntia* cacti.

As a result of restriction in source of raw materials, great fluctuation caused by weather effect and tedious process of extracting and purifying carminic acid from insects, the production mode of producing carminic acid from scale insects cannot be applied widely, and therefore, the market needs cheaper, simpler and more stable production modes. A microbial conversion method, owing to its fast biomass accumulation, short conversion time and the like, is gradually applied in industrial production to prepare various compounds. Frandsen et al (Heterologous production of the widely used natural food colorant carminic acid in *Aspergillus nidulans*, publication data: 2018) has constructed a synthetic pathway of semisynthetic carminic acid in *Aspergillus nidulans*. They have made expression of cyclase ZhuI, aromatase ZhuJ and OKS of Octaketide synthase 1 and C-glucosyltransferase UGT2 in *A. nidulans* and constructed the synthetic pathway of carminic acid. As *A. nidulans* itself has many gene clusters for the pathway to synthesize polyketides, key genes necessary to the synthetic pathway of carminic acid cannot be clearly analyzed in construction of the synthetic pathway of carminic acid in *A. nidulans*. In addition, as a result of defects in safety of *A. nidulans*, complexity in gene editing operation, generation of green conidia and the like, production of *A. nidulans* for synthesizing carminic acid is restricted.

*S. cerevisiae* has been widely applied to cell factories that synthesize various compounds, features clear genetic background and simple gene editing and genetic manipulation, and can tolerate low pH. Compared with prokaryotes, it has a cell pigment P450 enzyme of eucaryons. Furthermore, *S. cerevisiae* has been regarded as a safe strain capable of being used in industrial production all the time.

Summary

This application has dug out and analyzed the key gene necessary to the synthetic pathway of carminic acid so as to construct an entire synthetic pathway of carminic acid in *S. cerevisiae*, thereby facilitating the synthetic pathway to be of potential guiding value and guiding significance to development of synthetic biology.

4'-phosphopantetheinyl transferase npgA (NCBI Reference Sequence: XP_663744.1, the amino acid sequence thereof as set forth in SEQ ID NO.14) derived from *A. nidulans* is optimally synthesized according to a codon of *S. cerevisiae* and is genetically synthesized by Sangon Biotech (Shanghai) Co., Ltd., and the final nucleotide sequence is as set forth in SEQ ID NO.1. Octaketide synthase-encoding OKS (UniProtKB/Swiss-Prot: Q3L7F5.1, the amino acid sequence thereof as set forth in SEQ ID NO.15) derived from *Aloe arborescens* is optimally synthesized according to a codon of *S. cerevisiae* and is genetically synthesized by Sangon Biotech (Shanghai) Co., Ltd., and the final nucleotide sequence is as set forth in SEQ ID NO.2. Cyclase ZhuI (UniProtKB/Swiss-Prot: Q9F6D3, the amino acid sequence thereof as set forth in SEQ ID NO.16) derived from *Streptomyces* sp. R1128 and aromatase ZhuJ (UniProtKB/Swiss-Prot: Q9F6D2, the amino acid sequence thereof as set forth in SEQ ID NO.17) are optimally synthesized according to a codon of *S. cerevisiae* and are genetically synthesized by Sangon Biotech (Shanghai) Co., Ltd., and the final nucleotide sequences thereof are as set forth in SEQ ID NO.3 and SEQ ID NO.4. C-glucosyltransferase UGT2 (GenBank: ATL15304.1, the amino acid sequence thereof as set forth in SEQ ID NO.18) derived from *D. coccu* is optimally synthesized according to a codon of *S. cerevisiae* and are genetically synthesized by Sangon Biotech (Shanghai) Co., Ltd., and the final nucleotide sequence thereof is as set forth in SEQ ID NO.5. Monooxygenase aptC (NCBI Reference Sequence: X_663606.1, the amino acid sequence thereof as set forth in SEQ ID NO.19) derived from *A. nidulans* is optimally synthesized according to a codon of *S. cerevisiae* and are genetically synthesized by Sangon Biotech (Shanghai) Co., Ltd., and the final nucleotide sequence thereof is as set forth in SEQ ID NO.6.

The disclosure provides a recombinant bacterium which integratively expresses 4'-phosphopantetheinyl transferase on a genome of the original strain, and expresses octaketide synthase OKS, cyclase, aromatase, C-glucosyltransferase and monooxygenase, where GAL80 in the genome of the *S. cerevisiae* is knocked out.

In an embodiment, an ADY2 gene in the genome of the *S. cerevisiae* is knocked out, and a Gen ID of the ADY2 gene is 85036.

In an embodiment, the amino acid sequence of the 4'-phosphopantetheinyl transferase is as set forth in SEQ ID NO.14, the amino acid sequence of the octaketide synthase is as set forth in SEQ ID NO.15, the amino acid sequence of the C-glucosyltransferase is as set forth in SEQ ID NO.18, the amino acid sequence of the monooxygenase is as set forth in SEQ ID NO.19, the amino acid sequence of the cyclase is as set forth in SEQ ID NO.16, the amino acid sequence of the aromatase is as set forth in SEQ ID NO.17, the nucleotide sequence of the GAL80 is as set forth in SEQ ID NO.21, and the nucleotide sequence of the ADY2 gene is as set forth in SEQ ID NO.22.

In an embodiment, the octaketide synthase OKS, cyclase ZhuI, aromatase ZhuJ, C-glucosyltransferase UGT2 and monooxygenase aptC are integrated to a high copy site.

In an embodiment, the high copy site is Ty2Cons site.

In an embodiment, the nucleotide sequence that encodes the OKS of the Octaketide synthase 1 is as set forth in SEQ ID NO.2.

In an embodiment, the nucleotide sequence that encodes the cyclase ZhuI is as set forth in SEQ ID NO.3.

In an embodiment, the nucleotide sequence that encodes the aromatase ZhuJ is as set forth in SEQ ID NO.4.

In an embodiment, the nucleotide sequence that encodes the C-glucosyltransferase UGT2 is as set forth in SEQ ID NO.5.

In an embodiment, the nucleotide sequence that encodes the monooxygenase aptC is as set forth in SEQ ID NO.6.

In an embodiment, S. cerevisiae is taken as an original strain.

In an embodiment, GAL80 is knocked out in the genome of the S. cerevisiae, the Gene ID of the GAL80 is 854954, and the nucleotide sequence thereof is as set forth in SEQ ID NO.21.

The disclosure provides a method for producing carminic acid, where the carminic acid is produced by means of fermentation by taking the recombinant bacterium as a fermentation strain. The method includes:

(1) picking a single colony of the recombinant bacterium, and inoculating the single colony to a YNB culture medium without uracil for culture at 220 rpm for 24 h to obtain a seed solution;

(2) inoculating the seed solution to a fresh YNB culture medium according to 4% by volume of the YNB culture medium for culture for 48 h to obtain a cell; and (3) adding the cell into a YPD culture medium to be fermented for culture for no less than 96 h.

In an embodiment, in step (3), ethanol or acetic acid is added once every 24 h.

In an embodiment, an adding amount of the ethanol is 0.1% by volume of a reaction system.

In an embodiment, a concentration of the acetic acid is 50%, and an adding amount of the acetic acid is 0.1% by volume of the reaction system.

Preferably, a fermentation time in step (3) is 96 h.

Or, the recombinant bacterium subjected to enrichment culture in the YNB culture medium for 24 h is transferred to the YPD culture medium for culture for 72 h, 2 g/L pyruvic acid is added every 24 h, and the recombinant bacterium is fermented for 72-264 h.

In an embodiment, the recombinant bacterium is fermented for at least 168 h.

Preferably, the recombinant bacterium is fermented for 168-264 h.

The disclosure provides a method for synthesizing carminic acid by utilizing S. cerevisiae. 4'-phosphopantetheinyl transferase undergoes integrated expression in a genome of S. cerevisiae, and S. cerevisiae also expresses OKS, cyclase, aromatase, C-glucosyltransferase and monooxygenase.

In an embodiment, S. cerevisiae is a chassis cell C800, the GAL80 gene is knocked out in the chassis cell C800, and the Gene ID of the GAL80 gene is 854954.

In an embodiment, NCBI Reference Sequence of 4'-phosphopantetheinyl transferase is XP_663744.1, UniProtKB/Swiss-Prot of OKS is Q3L7F5.1 of the OKS, GenBank of C-glucosyltransferase ATL15304.1, and NCBI Reference Sequence of monooxygenase is XP_663606.1.

In an embodiment, the nucleotide sequence that encodes the cyclase ZhuI is as set forth in SEQ ID NO.3.

In an embodiment, the nucleotide sequence that encodes the aromatase ZhuJ is as set forth in SEQ ID NO.4.

In an embodiment, the nucleotide sequence that encodes the C-glucosyltransferase UGT2 is as set forth in SEQ ID NO.5.

In an embodiment, S. cerevisiae is used to produce carminic acid in a fermentation system containing pyruvic acid.

The disclosure further provides the recombinant bacterium, or the method for producing carminic acid, or an application of the method for synthesizing carminic acid by utilizing S. cerevisiae in preparation of products containing carminic acid.

The disclosure has the following beneficial effects:

The disclosure has constructed a recombinant plasmid pY26-CA pathway A based on a known synthetic pathway of carminic acid, deduced and dug out key gene necessary to synthesize carminic acid based on change of functional groups synthesized by carminic acid, and integrated the key gene npgA to a genome site to express based on a CRISPR-Cas9 technology, so as to obtain recombinant S. cerevisiae C800-npgA. Another key gene aptC of the synthetic pathway is constructed based on pY26-CA pathway A, so as to obtain a recombinant plasmid pY26-CA pathway B. The recombinant plasmids pY26-CA pathway A and pY26-CA pathway B are respectively expressed in recombinant S. cerevisiae C800 and recombinant S. cerevisiae C800-npgA, so as to construct recombinant S. cerevisiae CA-A1, CA-B1, CA-A2 and CA-B2 respectively. Through shake-flask fermentation and HPLC detection, carminic acid is not detected in the recombinant S. cerevisiae CA-A1, CA-B1 and CA-A2 and is detected in the recombinant S. cerevisiae CA-B2. Further verified by LCMS, the compound is carminic acid. The disclosure has analyzed the key gene necessary to synthesize carminic acid clearly, authenticated the process of the synthetic pathway of carminic acid and constructed the synthetic pathway of carminic acid in S. cerevisiae successfully. By means of the constructed recombinant S. cerevisiae, the yield of the fermented carminic acid can reach 52.7 μg/L. On this basis, OKS, cyclase, aromatase, C-glucosyltransferase and monooxygenase relevant to carminic acid are integrated to a high copy site, which can remarkably improve the yield of carminic acid. The yield of carminic acid can be increased to 2664.6 μg/L by optimizing fermentation conditions, and the fermentation time is shortened significantly.

DETAILED DESCRIPTION (I) Culture medium

Figure 1:
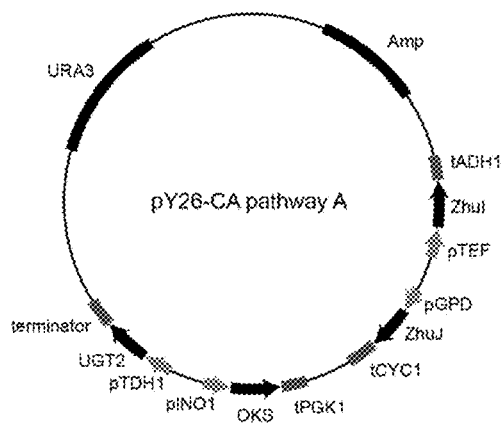
FIG. 1 is a plasmid profile of a recombinant vector pY26-CA pathway A.

An LB culture medium: a liquid culture medium was prepared from 10 g/L peptone, 5 g/L yeast powder and 10 g/L sodium chloride; and 20 g/L agar strip was added into the liquid culture medium to prepare an LB solid culture medium.

A YNB culture medium was prepared from 6.74 g/L yeast nitrogen base culture medium (without ammonium sulfate), 5 g/L ammonium sulfate, 20 g/L glucose and amino acids (5 g/L uracil, 10 g/L tryptophan, 10 g/L leucine and 10 g/L histidine, with proper amino acid deletion as needed).

An YPD culture medium was prepared from 20 g/L peptone, 10 g/L yeast powder and 20 g/L glucose.

(II) Solution

Preparation of 200 g/L pyruvic acid solution: 10 g of pyruvic acid was dissolved in 50 mL of ultrapure water.

(III) extraction and concentration of carminic acid: 5 mL of fermentation liquor was collected, isometric extract liquor was added (the extract liquor contained ethyl acetate, normal butanol and formic acid in a volume ratio of 69:30:1), the fermentation liquor was extracted to extract a fermentation product, an organic phase was collected and rotatory-dried by distillation, 1 ml of methanol (with 1% formic acid) was added to resuspend, and the organic phase passed through a membrane for HPLC analysis.

(IV) HPLC detection of carminic acid: by utilizing a chromatographic column (250*4.6 mm, 5 μm, Thermo-Fisher, MA, USA), a mobile phase was eluted with an aqueous solution (A) containing 0.1% formic acid and acetonitrile containing 0.1% formic acid at a flow rate of 1 mL/min by using an SPD-20A detector (SHIMADZU, Japan) under 40° C. detection condition, a detection wavelength being 494 nm, an elution condition being 0-20 min, 10%-100% B; 20-25 min, 100% B; 25-27 min, 100%-10% B; and 28-30 min, 10% B.

(V) lithium acetate conversion method:

A S. cerevisiae cell was streaked on an YPD panel and cultured at 30° C. for 3 days, a single colony was picked and inoculated to a 5 mL YPD liquid culture medium and was subjected to shaking culture at 30° C. at 220 rpm for 16 h, a bacterial solution was diluted till an $OD_{600}$ value was 0.3 and was then transferred to 50 mL of fresh YPD liquid culture media and was subjected to shaking culture at 30° C. at 220 rpm for about 5 h till the $OD_{600}$ value was 1.2-1.6.

The bacterial solution was collected and pre-cooled for 5 min on ice, the bacterial solution was centrifugalized at 5000*g for 5 min to collect bacterial cells, 25 mL of pre-cooled sterile water was added to resuspend the bacterial cells, the bacterial cells was centrifugalized at 5000*g for 5 min to collect precipitates, namely the bacterial cells, 1 mL of 0.1 mM lithium acetate was added into the bacterial cells to resuspend the bacterial cells, the bacterial cells was centrifugalized at 5000*g for 1 min to collect precipitates, namely the bacterial cells, 400 μL of 0.1 mM lithium acetate solutions was added into the bacterial cells to resuspend the bacterial cells, 50 μL of resuspended solutions was added into 240 μL of PEG3350, 36 μL of 1 mM lithium acetate solutions and 25 μL of 2 mg/mL ssDNA respectively, the mixture was subjected to shaking for 30 s to evenly mix the system, then the system was cultured at 30° C. for 30 min, the system was then subjected to hot shock in a 42° C. water bath after culture for 25 min, the system was centrifugalized at 5000*g for 1 min to collect bacterial cells, 1 mL of sterile resuspended bacterial cells was added, and 100 μL of bacterial cells resuspended solution was smeared to a corresponding YNP panel, and was cultured at 30° C. for 3 days.

(VI) Gibson assembling method:

A reaction system: 50 ng of DNA fragments was added, 100 ng of vectors was added, 5 μL of Gibson mix was added, and sterilize ultrapure water was added till the system was 10 μL.

A reaction condition: a reaction was performed at 50° C. for 60 min, and the system was placed on ice immediately after the reaction was finished to obtain a reaction solution. 10 μL of the reaction solutions was converted into an E. coli competent JM109.

(VII) Construction of chassis cell C800: the chassis cell with GAL80 knocked out was constructed based on S. cerevisiae CEN.PK2-1D cell (GAL80 was involved in galactose metabolic regulation, the constitutive expression of a GAL7 promoter could be realized after knockout instead of inducible expression); GAL80 (Gene ID:854954) was knocked out according to a principle of homologous recombination of yeast, and the C800 chassis cell was constructed by taking G418 as a selection marker. A specific construction process was seen in literature Promoter-Library-Based Pathway Optimization for Efficient (2S)-Naringenin Production From p-Coumaric Acid in S. cerevisiae, Song Gao, Hengrui Zhou, Jingwen Zhou, Jian Chen. J Agric Food Chem, 2020 Jun 24.

(VIII) Primer Star MasterMix was purchased from Takara.

Definition of ectopic expression and integrated expression:

Ectopic expression means the occurrence of gene expression in a tissue in which it is normally not expressed.

Integrated expression means expression that occurs when a gene is integrated into the genome.

Example 1: Construction of Expression Box of Related Gene of Synthetic Pathway of Carminic Acid By taking a synthetic sequence of Zhul (the nucleotide sequence was as set forth in SEQ ID NO.3) as a template, a primer pair F1/R1 was designed, PCR amplification was performed with the primer pair by using a high fidelity enzyme pfu enzyme of Primer Star MasterMix under the following conditions: predegeneration was performed at 95° C. for 3 min; 30 cycles was performed in an amplification stage according to 95° C., 10 s, 55° C., 10 s and 72° C., 30 s; extension was performed at 72° C. for 5 min, a PCR product was purified to obtain a fragment Zhul; and by taking a vector pY26 as a template, PCR amplification was performed with a primer pair F2/R2, and a product was purified. The fragment Zhul and the vector pY26 were recombined by means of the Gibson assembling method to obtain a recombinant vector, the recombinant vector was converted into *Escherichia coli* JM109, and a plasmid was extracted, sequenced and verified, so as to obtain a correct recombinant vector pY26-ZhuI.

By taking a synthetic sequence of ZhuJ (the nucleotide sequence was as set forth in SEQ ID NO.4) as a template, a primer pair F3/R3 was designed, PCR amplification was performed with the primer pair and a product was purified to obtain a fragment ZhuJ; by taking the vector pY26-ZhuI as a template, a primer pair F4/R4 was designed, PCR amplification was performed with the primer pair and a product was purified to obtain a fragment of the vector pY26-ZhuI. The fragment ZhuJ and the vector pY26-ZhuI were recombined by means of the Gibson assembling method to construct a recombinant vector pY26-ZhuI-ZhuJ, the recombinant vector pY26-ZhuI-ZhuJ was converted into *E. coli* JM109, and a plasmid was extracted, sequenced and verified, so as to obtain a correct recombinant vector pY26-ZhuI-ZhuJ.

By taking a synthetic sequence of OKS (the nucleotide sequence was as set forth in SEQ ID NO.2) as a template, PCR amplification was performed with a primer pair F5/R5 and a product was purified to obtain a fragment OKS; by taking a promoter pINO1 (the nucleotide sequence was as set forth in SEQ ID NO.7), PCR amplification was performed with a primer pair F6/R6 and a product was purified to obtain a fragment pINO1; by taking a terminator tPGK1 (the nucleotide sequence was as set forth in SEQ ID NO.8) as a template, PCR amplification was performed with a primer pair F7/R7 and a product was purified to obtain a fragment tPGK1. By taking a pMD19T-simple as a template, PCR amplification was performed with a primer pair F8/R8 and a product was purified to obtain a vector fragment of the pMD19T-simple. The OKS, pINO1, tPGK1 and vector pMD19T-simple were assembled by means of the Gibson assembling method to obtain a vector pMD19T-pINO1-OKS-tPGK1, the obtained vector was converted into *E. coli* JM109, and was sequenced and verified, so as to obtain a correct recombinant vector pMD19T-pINO1-OKS-tPGK1.

By taking a synthetic sequence of UGT2 (the nucleotide sequence was as set forth in SEQ ID NO.5) as a template, PCR amplification was performed with a primer pair F9/R9 and a product was purified to obtain a fragment UGT2; by taking the promoter pTDH1 (the nucleotide sequence was as set forth in SEQ ID NO.9) as a template, PCR amplification was performed with a primer pair F10/R10 and a product was purified to obtain a fragment pTDH1; by taking a terminator ter-pGAL7 (the nucleotide sequence was as set forth in SEQ ID NO.10) as a template, PCR amplification was performed with a primer pair F11/R11 and a product was purified to obtain a fragment ter-pGAL7; and by taking pMD19T-simple as a template, PCR amplification was performed with a primer pair F12/R12 and a product was purified to obtain a linearized vector pMD19T-simple. The fragments UGT2, pTDH1 and ter-pGAL7 and the vector pMD19T-simple were assembled by means of the Gibson assembling method to obtain a recombinant vector pMD19T-pTDH1-UGT2-ter-pGAL7, the obtained recombinant vector was converted into *E. coli* JM109, and a plasmid was extracted, sequenced and verified, so as to obtain a correct recombinant vector pMD19T-pTDH1-UGT2-ter-pGAL7.

By taking a synthetic sequence of aptC (the nucleotide sequence was as set forth in SEQ ID NO.6) as a template, PCR amplification was performed with a primer pair F13/R13 and a product was purified to obtain a fragment aptC; by taking a terminator tVPS13 (the nucleotide sequence was as set forth in SEQ ID NO.11) as a template, PCR amplification was performed with a primer pair F14/R14 and a product was purified to obtain a fragment tVPS13; and by taking pMD19T-simple as a template, PCR amplification was performed with a primer pair F15/R15 and a product was purified to obtain a linearized vector pMD19T-simple. The fragments aptC and tVPS13 and the vector pMD19T-simple were assembled by means of the Gibson assembling method to obtain a recombinant vector pMD19T-aptC-tVPS13, and the obtained recombinant vector was converted into *E. coli* JM109, and was sequenced and verified, so as to obtain a correct recombinant vector pMD19T-aptC-tVPS13.

By taking a synthetic sequence of npgA (the nucleotide sequence was as set forth in SEQ ID NO.1) as a template, PCR amplification was performed with a primer pair F16/R16 and a product was purified to obtain a fragment npgA; by taking the promoter pGAL1 as a template, PCR amplification was performed with a primer pair F17/R17 and a product was purified to obtain a fragment pGAL1; and by taking a vector pY26 as a template, PCR amplification was performed with a primer pair F18/R18 and a product was purified to obtain a linearized vector pY26. The fragments npgA and pGAL1 and the vector pY26 were recombined by means of the Gibson assembling method to obtain a recombinant vector pY26-pGAL1-npgA, and the obtained recombinant vector was converted into *E. coli* JM109, and was sequenced and verified, so as to obtain a correct recombinant vector pY26-pGAL1-npgA.

TABLE 1 primers used

| Primers | Sequences 5'- 3' (Underlined parts are regions of homologous arms) | SEQ ID NO |
|---|---|---|
| F1 | GCGAAGAATTTTAAGCAGTAACAGTACCAACACCACCAGCAG | 23 |
| R1 | TCTAGAACTAATGAGACATGTTGAACATACTGTTACTGTCG | 24 |
| F2 | CATGTCTCATTAGTTCTAGAAAACTTAGATTAGATTGCTATGCTTTCTTTCT | 25 |
| R2 | TACTGCTTAAAATTCTTCGCCAGAGGTTTGGTCAA | 26 |
| F3 | TTCGACGGATATGTCTGGTAGAAAGACTTTCTTGGATTTGT | 27 |
| R3 | GTGACATAACTTAATCTTCTTCTTCTTGTTCGAAAACAGCAACAAC | 28 |
| F4 | AGAAGATTAAGTTATGTCACGCTTACATTCACGCC | 29 |
| R4 | TACCAGACATATCCGTCGAAACTAAGTTCTGGTGT | 30 |

TABLE 1-continued primers used

| Primers | Sequences 5'- 3' (Underlined parts are regions of homologous arms) | SEQ ID NO |
|---|---|---|
| F5 | TCAATTCAATTTACATCAATGGCAAAGAATGCAACAAAATAGTTTC | 31 |
| R5 | AAGAAGTAACATGTCCTCTTTGTCCAACGCTTCC | 32 |
| F6 | AAGAGGACATGTTACTTCTTTTTCACTGGAAAAAAAGGGAATGAAAC | 33 |
| R6 | TTCGACGATTGAAGACGATGAGGCCGGTG | 34 |
| F7 | TCCAGAGATTTTTGAACCTCATTGTATTTTACGGAAAAGAATATCATACTC | 35 |
| R7 | ATTGATGTAAATTGAATTGAATTGAAATCGATAGATCAATTTTTTTCTTTTCTCTTTC | 36 |
| F8 | CATCGTCTTCAATCGTCGAACGGCAGGC | 37 |
| R8 | GAGGTTCAAAAATCTCTGGAAGATCCGCGC | 38 |
| F9 | ACAAAACAAAATGGAATTCAGATTATTGATTTTGGCTTTATTCTCTG | 39 |
| R9 | AGCTGGCAAATTAGTTCTTCTTCAACTTTTCAGACTTAGAAGAAGACC | 40 |
| F10 | TCCAGAGATTGAAACCACACCGTGGGGC | 41 |
| R10 | TGAATTCCATTTTGTTTTGTGTGTAAATTTAGTGAAGTACTGTTTTTTGTG | 42 |
| F11 | GAAGAACTAATTTGCCAGCTTACTATCCTTCTTGAAAATATGC | 43 |
| R11 | TTCGACGATTTTTTGAGGGAATATTCAACTGTTTTTTTTTATCATGTTGATG | 44 |
| F12 | TCCCTCAAAAAATCGTCGAACGGCAGGC | 45 |
| R12 | GTGTGGTTTCAATCTCTGGAAGATCCGCGC | 46 |
| F13 | TCCAGAGATTATGACTTTGCCAGTTTTGATTATTGGTG | 47 |
| R13 | TCATATGTGATTAAGCTCTCATCTTTTGCTTTTCAGCGA | 48 |
| F14 | GAGAGCTTAATCACATATGAAAGTATATACCCGCTTTTGTACAC | 49 |
| R14 | TTCGACGATTGAGAGTAGACTTTTTCTGTGAAATTTAATGAGTTTTTGT | 50 |
| F15 | GTCTACTCTCAATCGTCGAACGGCAGGC | 51 |
| R15 | GCAAAGTCATAATCTCTGGAAGATCCGCGC | 52 |
| F16 | AAAAACTATAATGGTTCAAGATACTTCTTCAGCTTCTACATC | 53 |
| R16 | AATTACATGATTAAGATAAACAATTACAAACACCTGTAGCACATGG | 54 |
| F17 | TAACTGATCATTATATTGAATTTTCAAAAATTCTTACTTTTTTTTGGATGGACG | 55 |
| R17 | CTTGAACCATTATAGTTTTTTCTCCTTGACGTTAAAGTATAGAGGTATATTAACAAT | 56 |
| F18 | TTTATCTTAATCATGTAATTAGTTATGTCACGCTTACATTCACG | 57 |
| R18 | TTCAATATAATGATCAGTTAACTCCGGACCGC | 58 |

Example 2: Construction of Vector A of Synthetic Pathway of Carminic Acid

By taking a vector pMD19T-pINO1-OKS-tPGK1 constructed in Example 1 as a template, PCR amplification was performed with a primer pair F19/R19 and a product was purified to obtain a fragment pINO1-OKS-tPGK1; by taking pMD19T-pTDH1-UGT2-ter-pGAL7 constructed in Example 1 as a template, PCR amplification was performed with a primer pair F20/R20 and a product was purified to obtain a fragment pTDH1-UGT2-ter-pGAL7; and by taking pY26-Zhul-ZhuJ constructed in Example 1 as a template, PCR amplification was performed with a primer pair F21/R21 and a product was purified to obtain a vector fragment pY26-Zhul-ZhuJ. The fragments pINO1-OKS-tPGK1 and pTDH1-UGT2-ter-pGAL7 and the vector pY26-Zhul-ZhuJ were recombined by means of the Gibson assembling method to obtain a recombinant vector, and the obtained recombinant vector was converted into *E. coli* JM109, and was sequenced and verified, so as to obtain a correct recombinant vector pY26-CA pathway A (pY26-Zhul-ZhuJ-pINO1-OKS-tPGK1-pTDH1-UGT2-ter-pGAL7) (see FIG. 1)

TABLE 2 primers used

| Primers | Sequences 5'-3' (Underlined parts are regions of homologous arms) | SEQ ID NO. |
|---|---|---|
| F19 | <u>GTCGTATTACTTTGAACCTCATTGTATTTTACGGAAAAGAATAT</u>CATACTC | 59 |
| R19 | <u>GTGTGGTTTCGAGGCTTGTCAGTACATCAGCGAT</u> | 60 |
| F20 | GACAAGCCTCGAAACCACACCGTGGGGC | 61 |
| R20 | <u>GTGAGCGCGCTTTTGAGGGAATATTCAACTGTTTTTTTTTATCAT</u>GTTGATG | 62 |
| F21 | <u>TCCCTCAAAAGCGCGCTCACTGGCC</u> | 63 |
| R21 | <u>GAGGTTCAAAGTAATACGACTCACTATAGGGCGAATTGG</u> | 64 |

Example 3: Construction of a Vector B of a Synthetic Pathway of Carminic Acid

Figure 2:
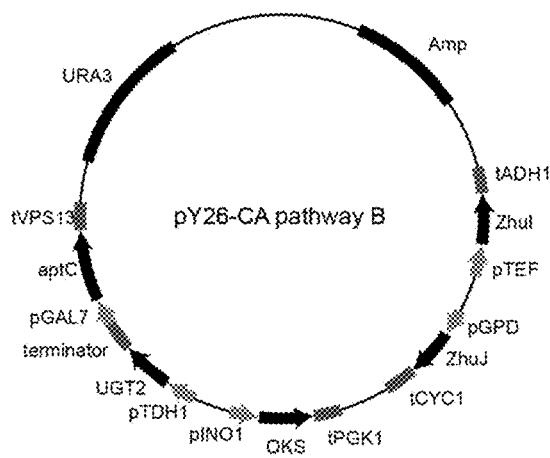
FIG. 2 is a plasmid profile of a recombinant vector pY26-CA pathway B.

By taking a pMD19T-aptC-tVPS13 constructed in Example 1 as a template, PCR amplification was performed with a primer pair F22/R22 and a product was purified to obtain a fragment aptC-tVPS13; by taking pY26-CA pathway A as a template, PCR amplification was performed with a primer pair F23/R23 to obtain a linearized vector pY26-CA pathway A. The fragment aptC-tVPS13 and the vector pY26-CA pathway A were recombined by means of the Gibson assembling method to obtain a recombinant vector, and the obtained recombinant vector was converted into *E. coli* JM109, and was sequenced and verified, so as to obtain a correct recombinant vector pY26-CA pathway B (pY26-ZhuI-ZhuJ-pINO1-OKS-tPGK1-pTDH1-UGT2-ter-pGAL7-aptC-tVPS13) (see FIG. 2).

TABLE 3 primers used

| Primers | Sequences 5'-3' (Underlined parts are regions of homologous arms) | SEQ ID NO |
|---|---|---|
| F22 | <u>TCCCTCAAAAATGACTTTGCCAGTTTTGATTATTGGTG</u> | 65 |
| R22 | <u>GTGAGCGCGCGAGAGTAGACTTTTTCTGTGAAATTTAATGAGTTTTTGTTC</u> | 66 |
| F23 | <u>GTCTACTCTCGCGCGCTCACTGGCC</u> | 67 |
| R23 | <u>GCAAAGTCATTTTTGAGGGAATATTCAACTGTTTTTTTTTATCATGTTG</u> | 68 |

Example 4: Analysis of Synthetic Pathway of Carminic Acid

The recombinant vector pY26-CA pathway A and the recombinant vector pY26-CA pathway B were converted into the chassis cell C800 by means of a lithium acetate chemical conversion method, and were cultured on a YNB panel without uracil at 30° C. for 3 days till a single colony grew; the single colony was picked and cultured in a YNB culture medium without uracil at 220 rpm for 24 h; and the following primer pair was designed:
F24: TCATGTT-TATGGTAGAACTAGAGAATACTTGCAATT-AGAAAAG; (SEQ ID NO:69)
R24: GTTTTGTGGGATTGTGGTAACATGGTC (SEQ ID NO:70).

Figure 3:
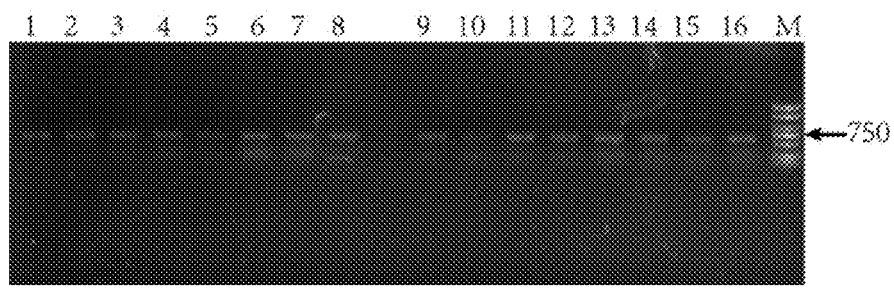
FIG. 3 is a gel electrophoretogram of colony PCR verification of recombinant S. cerevisiae CA-A1.
Figure 4:
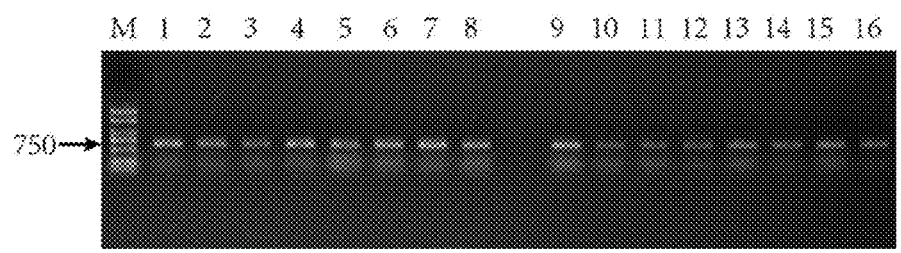
FIG. 4 is a gel electrophoretogram of colony PCR verification of recombinant S. cerevisiae CA-B1.

The cultured bacterial solution was subjected to PCR verification with the primer pair, and a correct clone was picked to construct recombinant *S. cerevisiae* CA-A1 (expressing pY26-CA pathway A based on the chassis cell C800, see FIG. 3) and CA-B1 (expressing pY26-CA pathway B based on the chassis cell C800, see FIG. 4). The recombinant *S. cerevisiae* CA-A1 and CA-B1 were streaked on the YNB panel without uracil and cultured at 30° C. for 3 days till a single colony grew; the single colony was picked and cultured in the YNB culture medium without uracil at 220 rpm for 24 h, and was transferred to the YPD culture medium, 200 g/L pyruvic acid at 1 mL/100 mL was added every 24 h after 72 h, sampling was performed respectively at 72 h, 120 h, 168 h, 216 h and 264 h, the bacterial solution was extracted, and an HPLC result showed that carminic acid products were not detected in the recombinant *S. cerevisiae* CA-A1 and CA-B1.

Example 5: Integrative Expression of npgA in Genome of *S. cerevisiae* based on CRISPR-Cas9 Technology A npgA expression box is integrated to a ADY2 site of the genome to express by utilizing the CRISPR-Cas9 technology, and the following primer pair was designed by taking pY26-pGAL1-npgA as a template:
F25: ATGTCTGACAAGGAACAAACGAGCGGAAACACA-GATTTGGAGAATGCACCAGCAGGATACTTATATTG AATTTTCAAAAATTCTTACTTTTTTTTTGGA (SEQ ID NO:71);
R25: CATAGCACAACCGACGACAACATTAGGAACAGT-GATCCCTTGCGCTCTCGCATT-GAACGTAATACGACTC ACTATAGGGCGAATTGG (SEQ ID NO:72).

Figure 5:
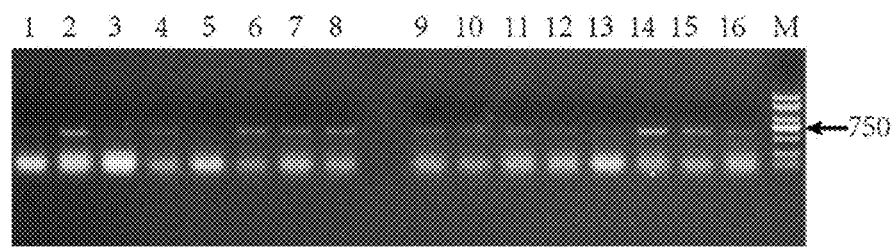
FIG. 5 is a gel electrophoretogram of colony PCR verification of recombinant S. cerevisiae C800-npgA.

PCR amplification was performed with the primer pair and a product was purified to obtain a fragment UP60- pGAL1-npgA-ter-DOWN60. The UP60-pGAL1-npgA-ter-DOWN60, the p414-TEF1p-Cas9-CYC1t plasmid and 20nt sgRNA plasmid pRS426-ADY2-sgRNA containing ADY2 (the nucleotide sequence thereof was as set forth in SEQ ID NO.12) were converted into the chassis cell C800 by means of a lithium acetate chemical conversion method, and were cultured on a YNB panel without uracil and tryptophan at 30° C. for 3 days till a single colony grew; the single colony was picked and cultured in a YNB culture medium without uracil and tryptophan at 220 rpm for 24 h; and the following primer pair was designed:
F26: GCTACTGCTGCAAGAGGTGG (SEQ ID NO:73),
R26: CATGGTACAAACGGTTAAACCAAACGT (SEQ ID NO:74).
PCR verification was performed on the cultured bacterial solution with the primer pair, a correct clone was picked, and a plasmid pRS426-ADY2-sgRNA was eliminated through continuous passage culture and spotting verification of plasmid elimination so as to construct the recombinant S. cerevisiae C800-npgA (see FIG. 5).

Example 6: Identification of Synthetic Pathway of Carminic Acid

The correctly sequenced recombinant vector pY26-CA pathway A and the recombinant vector pY26-CA pathway B were respectively converted into the chassis cell C800 by means of a lithium acetate chemical conversion method, and were cultured on a YNB panel without uracil at 30° C. for 3 days till a single colony grew; the single colony was picked and cultured in a YNB culture medium without uracil at 220 rpm for 24 h; and the following primer pair was designed:
F27: TCATGTTTATGGTAGAACTAGAGAATACTTGCAATTAGAAAAG (SEQ ID NO:75);
R27: GTTTTGTGGGATTGTGGTAACATGGTC (SEQ ID NO:76).

Figure 6:
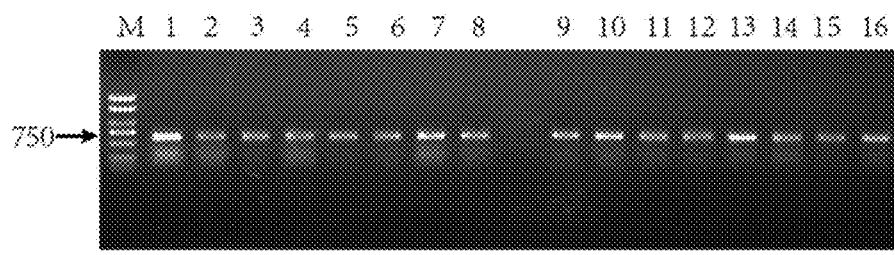
FIG. 6 is a gel electrophoretogram of colony PCR verification of recombinant S. cerevisiae CA-A2.
Figure 7:
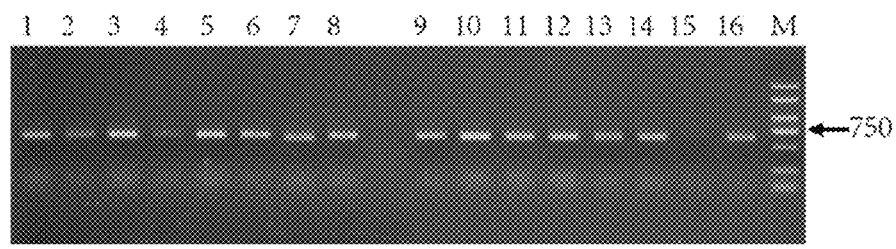
FIG. 7 is a gel electrophoretogram of colony PCR verification of recombinant S. cerevisiae CA-B2.
Figure 8A:
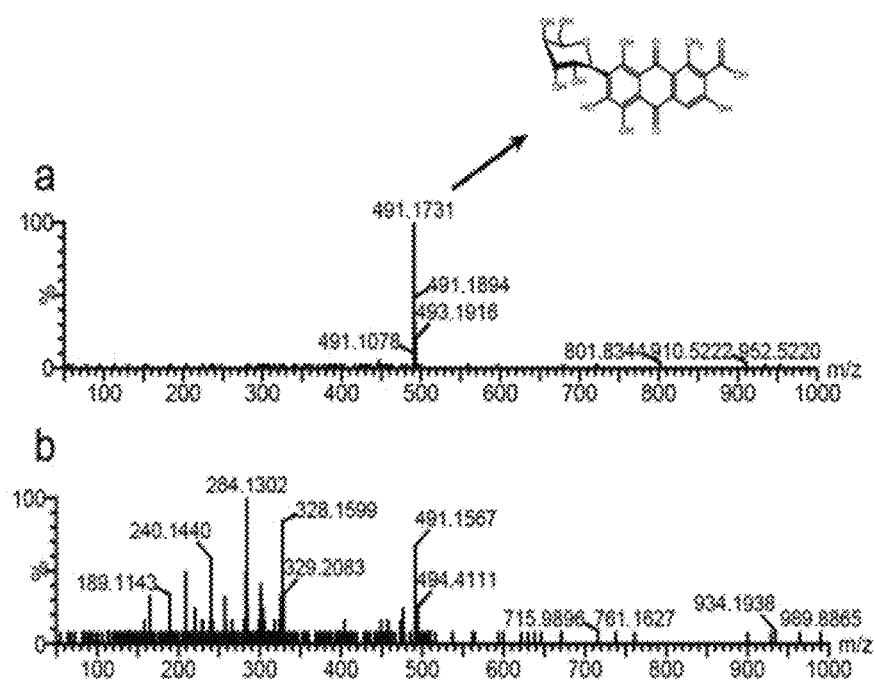
FIG. 8A is an LCMS graph of recombinant S. cerevisiae CA-B2 and a carminic acid standard substance, where a is the carminic acid standard substance and b is fermentation liquor of the recombinant S. cerevisiae CA-B2.
Figure 8B:
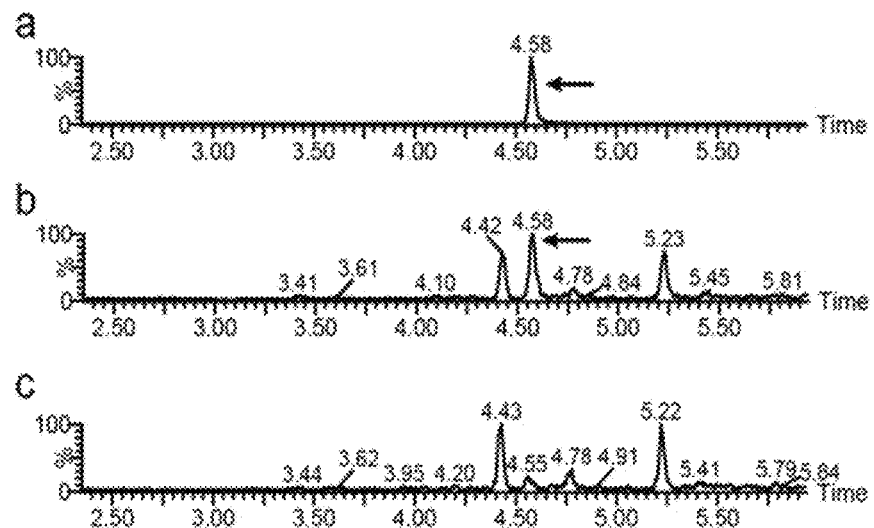
FIG. 8B is an LCMS graph of recombinant S. cerevisiae CA-B2, a control group C800-npgA and a carminic acid standard substance, where a is the carminic acid standard substance, b is fermentation liquor of the recombinant S. cerevisiae CA-B2, and c is an original strain C800-npgA.
Figure 9:
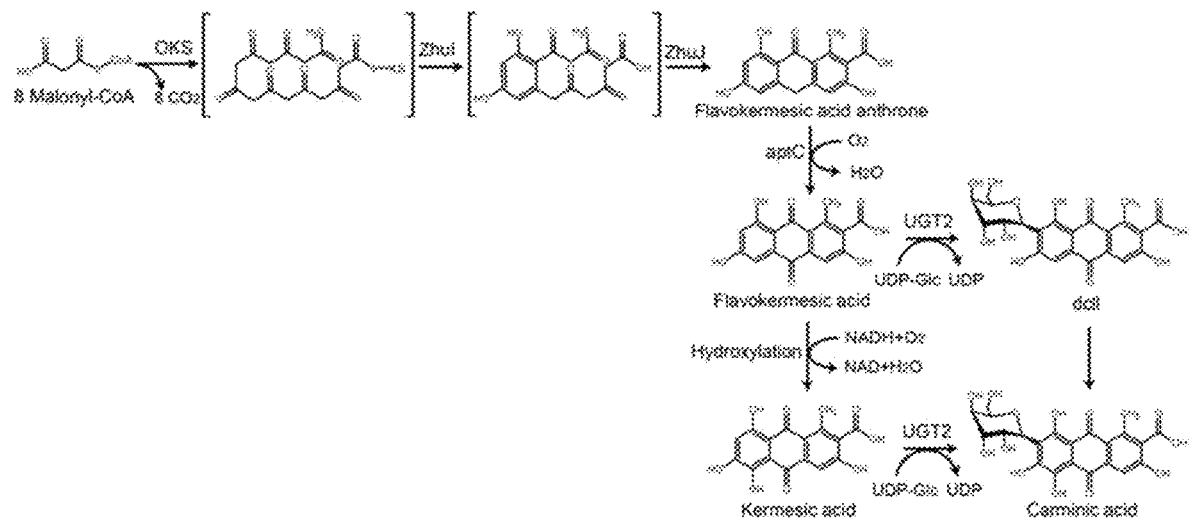
FIG. 9 is a synthetic pathway diagram of synthesizing carminic acid by S. cerevisiae.

The cultured bacterial solution was subjected to PCR verification with the primer pair, and a correct clone was picked to construct recombinant S. cerevisiae CA-A2 (expressing pY26-CA pathway A based on the chassis cell C800-npgA, see FIG. 6) and CA-B2 (expressing pY26-CA pathway B based on the chassis cell C800-npgA, see FIG. 7). The recombinant S. cerevisiae CA-A2 and CA-B2 were streaked on the YNB panel without uracil and cultured at 30° C. for 3 days till a single colony grew; the single colony was picked and cultured in the YNB culture medium without uracil at 220 rpm for 24 h, and was transferred to the YPD culture medium, 200 g/L pyruvic acid at 1 mL/100 mL was added every 24 h after 72 h, sampling was performed respectively at 72 h, 120 h, 168 h, 216 h and 264 h, the bacterial solution was extracted, and an HPLC result showed that carminic acid products were not detected in the recombinant S. cerevisiae CA-A2, and carminic acid products were detected in the recombinant S. cerevisiae CA-B2. In order to further confirm that the compound is carminic acid, LCMS analysis was performed, identifying that the substance was carminic acid (see FIG. 8). Therefore, expressing npgA, ZhuI, ZhuJ, OKS, UGT2 and aptC in S. cerevisiae can synthesize carminic acid.

TABLE 4

| Yield of carminic acid | | | | | |
|---|---|---|---|---|---|
| | 72 h | 120 h | 168 h | 216 h | 264 h |
| Carminic acid (μg/L) | 0 | 0 | 24.7 | 39.8 | 52.7 |

Figure 10:
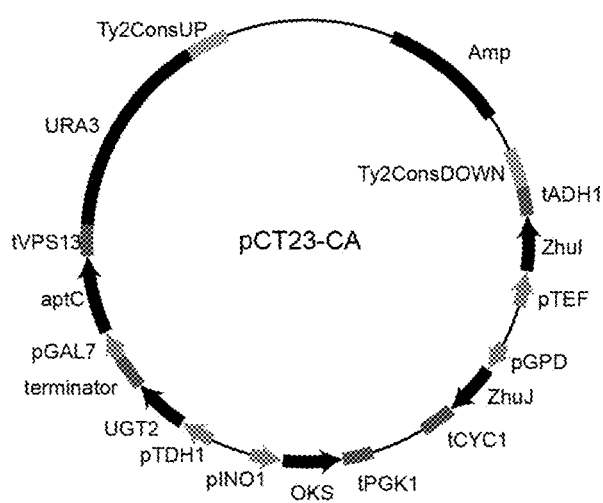
FIG. 10 is a plasmid profile of pCT23-CA.

Example 7: Construction of High Copy Integrative Expression Box of Synthetic Pathway of Carminic Acid By taking a vector pCT23-EGFP (the nucleotide sequence thereof was as set forth in SEQ ID NO.13) constructed in the lab as a template, PCR amplification was performed with a primer pair F28/R28 and a PCR product was purified to obtain a fragment pCT23; by taking pY26-CA pathway B constructed in Example 3 as a template, PCR amplification was performed with a primer pair F29/R29 and a PCR product was purified to obtain a fragment pTEF-ZhuI-tADH1-pGPD-ZhuJ-tCYC1-pINO1-OKS-tPGK1-pTDH1-UGT2-ter-pGAL7-aptC-tVPS13 of an expression box of a synthetic pathway of carminic acid; the fragments pCT23 and pTEF-ZhuI-tADH1-pGPD-ZhuJ-tCYC1-pINO1-OKS-tPGK1-pTDH1-UGT2-ter-pGAL7-aptC-tVPS13 were recombined by means of the Gibson assembling method to obtain a recombinant vector, and the obtained recombinant vector was converted into E. coli JM109, and was sequenced and verified, so as to obtain a correct recombinant vector pCT23-CA (pCT23-pTEF-ZhuI-tADH1-pGPD-ZhuJ-tCYC1-pINO1-OKS-tPGK1-pTDH1-UGT2-ter-pGAL7-aptC-tVPS13) (a plasmid profile was shown in FIG. 10).

TABLE 5

| | primers used | |
|---|---|---|
| Primers | Sequences 5'-3' (Underlined parts are regions of homologous arms) | SEQ ID NO |
| F28 | AAAAAGTCTACTCTCTTACAAATGAATAACGAAATGAGACAAAGAAGAGAAC | 77 |
| R28 | AGCTGGCGTAATAGCGTTAATATTCATTGATCCTATTACATTATCAATCCTTGCGTTTCA | 78 |
| F29 | TCAATGAATATTAACGCTATTACGCCAGCTGAATTGGAGC | 79 |
| R29 | GTTATTCATTTGTAAGAGAGTAGACTTTTTCTGTGAAATTTAATGAGTTTTTGTTCAC | 80 |

Example 8: Construction of High Copy Integratively Expressed Strain of Synthetic Pathway of Carminic Acid Based on a homologous recombination capacity of yeast itself, the expression box of the synthetic pathway of carminic acid was integrated to a multi-copy site, Ty2Cons site, of *S. cerevisiae* through integrated homologous arms upstream and downstream Ty2Cons, and the following primer pair was designed:

F30:
GTGTCCGCGCTGAGGGTTAATGGCGCGCCGCGGCCGCCCGCGGTGTTGGAATAAAAATCAACTA TCATCTACTAACTAGTATTTAC (SEQ ID NO:81),

R30:
GTATAGGAACTTCACTTCAGGTCTGAGTGCGGCCGCAGATCTGAGAATGTGGATTTTGATGTAATT GTTGGGATTCCATTTTTAATAAG (SEQ ID NO:82).

Figure 11A:
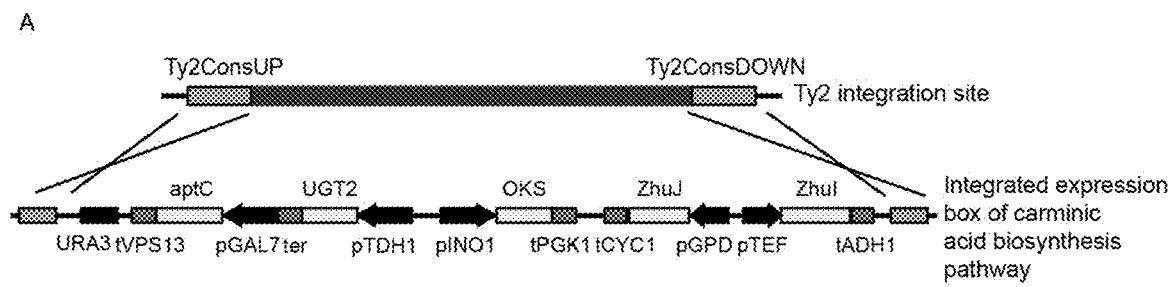
FIG. 11A is an expression box of a synthetic pathway of carminic acid.
Figure 11B:
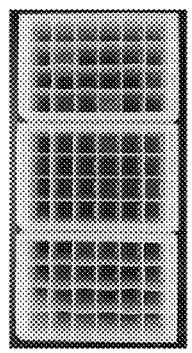
FIG. 11B is a fermentation result diagram of 24-deep well plates.
Figure 11C:
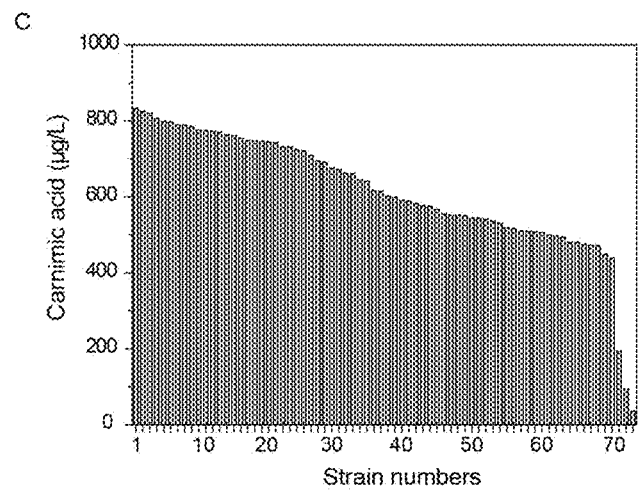
FIG. 11C is a yield diagram of carminic acid.

PCR amplification was performed on the plasmid pCT23-CA constructed in Example 7 with the primer pair and a product was purified to obtain a fragment Ty2ConsUP-pTEF-Zhu1-tADH1-pGPD-ZhuJ-tCYC1-pINO1-OKS-tPGK1-pTDH1-UGT2-ter-pGAL7-aptC-tVPS13-URA3-Ty2ConsDown. The fragment Ty2ConsUP-pTEF-Zhu1-tADH1-pGPD-ZhuJ-tCYC1-pINO1-OKS-tPGK1-pTDH1-UGT2-ter-pGAL7-aptC-tVPS13-URA3-Ty2ConsDown was converted into the chassis cell C800-npgA by means of a lithium acetate chemical conversion method, and was cultured on a YNB panel without uracil at 30° C. for 3 days till a single colony grew; the single colony was picked and cultured in a 24-deep well plate with 4 mL of YNB culture media at 220 rpm for 216 h; the bacterial solution was extracted, detected by HPLC, and screened to obtain a high-yield strain CA1. The high-yield strain CA1 was re-screened on a shake flask (the producing strain CA1 for carminic acid was streaked on the YNB panel without uracil, and cultured at 30° C. for 3 days till a single colony grew; the single colony was picked and inoculated to 5 mL of YNB culture media without uracil, cultured at 220 rpm for 24 h, 2 mL of seed solutions was transferred to 30 mL of YPD culture media, and was cultured at 220 rpm for 216 h), and the highest yield of carminic acid could reached 2245.7 μg/L (see FIG. 11).

Example 9: Optimization of Fermentation Condition of Producing Strain of Carminic Acid The fermentation conditions were optimized based on the producing strain CA1 of carminic acid, so that the fermentation period was shortened.

A fermentation condition A: the acid producing strain CA1 of carminic was streaked on the YNB panel without uracil, and cultured at 30° C. for 3 days till a single colony grew; the single colony was picked and inoculated to 5 mL of YNB culture media without uracil, cultured at 220 rpm for 24 h, 2 mL of seed solutions was transferred to 30 mL of YPD culture media, and was cultured for 216 h at 220 rpm.

A fermentation condition B: the producing strain CA1 of carminic acid was streaked on the YNB panel without uracil, and cultured at 30° C. for 3 days till a single colony grew; the single colony was picked and inoculated to 5 mL of YNB culture media without uracil, cultured at 220 rpm for 24 h, and 2 mL of seed solutions was transferred to 50 mL of YPD culture media, was cultured in the YNB culture medium for 48 h for cell enrichment, then resuspended in 10 mL of YPD culture media to ferment, and cultured at 220 rpm for 96 h.

A fermentation condition C: the producing strain CA1 of carminic acid was streaked on the YNB panel without uracil, and cultured for 3 days at 30° C. till a single colony grew; the single colony was picked and inoculated to 5 mL of YNB culture media without uracil, cultured for 24 h at 220 rpm, 2 mL of seed solutions was transferred to 50 mL of YPD culture media, was cultured for 48 h in the YNB culture medium after cells were enriched and resuspended in 10 mL of YPD culture media to ferment, and it was cultured at 220 rpm for 96 h under a condition of adding 0.1% ethanol every 24 h.

A fermentation condition D: the producing strain CA1 of carminic acid was streaked on the YNB panel without uracil, and cultured at 30° C. for 3 days till a single colony grew; the single colony was picked and inoculated to 5 mL of YNB culture media without uracil, cultured for 24 h at 220 rpm, and 2 mL of seed solutions was transferred to 50 mL of YPD culture media, was cultured in the YNB culture medium for 48 h for cell enrichment, then resuspended in 10 mL of YPD culture media to ferment, and cultured at 220 rpm for 96 h under a condition of adding 0.1% of 50% acetic acid every 24 h.

Figure 12:
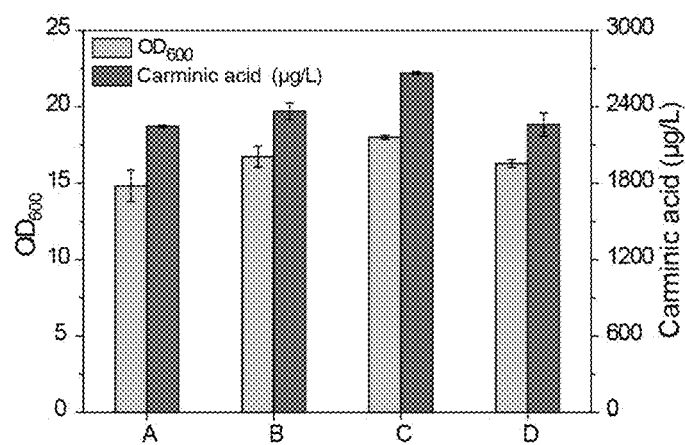
FIG. 12 is a yield diagram of carminic acid under different fermentation conditions.

Yields of carminic acid in the fermentation conditions B, C and D were higher than that of carminic acid in the fermentation condition A. Under the condition of supplementing 0.1% ethanol (the fermentation condition C), after fermentation in YPD for 96 h, the yield of carminic acid was 2664.6 μg/L. Compared with the fermentation condition A (2245.7 μg/L, the fermentation period 216 h), the yield of carminic acid was increased by 18.7%, and the period was shortened by half, thereby greatly saving the time cost and increasing the yield of carminic acid (see FIG. 12).

Although disclosed with preferred examples above, the disclosure is not limited by the examples. Any of those skilled in the art may make various alternations and modifications without departing the spirit and scope of the disclosure. Therefore, the scope of protection of the disclosure should be subject to the scope of the disclosure as defined in the claims.

---

What is claimed is:

1. A recombinant *Saccharomyces cerevisiae* (*S. cerevisiae*), comprising a genome having integrated therein a gene encoding 4'-phosphopantetheinyl transferase from *Aspergillus nidulans*
wherein octaketide synthase, cyclase, aromatase, C-glucosyltransferase and monooxygenase undergo ectopic expression or integrated expression in the recombinant *S. cerevisiae*,
wherein the amino acid sequence of the 4'-phosphopantetheinyl transferase is as set forth in SEQ ID NO:14,
wherein the amino acid sequence of the octaketide synthase is as set forth in SEQ ID NO:15
wherein the amino acid sequence of the C-glucosyltransferase is as set forth in SEQ ID NO:18,
wherein the amino acid sequence of the monooxygenase is as set forth in SEQ ID NO:19
wherein the amino acid sequence of the cyclase is as set forth in SEQ ID NO:16, and
wherein the amino acid sequence of the aromatase is as set forth in SEQ ID NO:17.

2. The recombinant *S. cerevisiae* according to claim 1, wherein a GAL80 gene in the genome is knocked out, and the nucleotide sequence of the GAL80 gene is as set forth in SEQ ID NO:21.

3. The recombinant *S. cerevisiae* according to claim 1, wherein an ADY2 gene in the genome of the *S. cerevisiae* is knocked out, and the nucleotide sequence of the ADY2 gene is as set forth in SEQ ID NO:22.

4. The recombinant *S. cerevisiae* according to claim 1, wherein the octaketide synthase, cyclase, aromatase, C-glucosyltransferase, and monooxygenase are integrated to a high copy site.

5. The recombinant *S. cerevisiae* according to claim 4, wherein the high copy site is a Ty2Cons site.

6. A method for producing carminic acid, which comprises fermenting the recombinant *S. cerevisiae* according to claim 1 in a cell culture medium under conditions that cause expression of the 4'-phosphopantetheinyl transferase, octaketide synthase, cyclase, aromatase, C-glucosyltransferase and monooxygenase.

7. The method according to claim 6, which comprises:
enriching and culturing the recombinant *S. cerevisiae* in YNB medium for 20 to 24 hours to obtain enriched cells;
transferring the enriched cells to YPD medium;
culturing for 70 to 76 hours;
adding pyruvic acid every 20 to 24 hours; and
fermenting for 72 to 264 hours;
or,
enriching the recombinant *S. cerevisiae* in YNB medium for 40 to 48 hours to obtain enriched cells;
adding the enriched cells to YPD medium for fermentation, and
adding ethanol or acetic acid every 20 to 24 hours.

8. The method according to claim 7, wherein the pyruvic acid is added in an amount of 1 to 5 g per liter of medium.

9. The method according to claim 7, wherein a concentration of the ethanol is 0.1% to 0.5%.

10. The method according to claim 7, wherein a concentration of the acetic acid is 45% to 55%, and an addition amount of the acetic acid is 0.1% to 0.5% by volume of the medium.

* * * * *